US011011200B2

(12) United States Patent
Uetake et al.

(10) Patent No.: US 11,011,200 B2
(45) Date of Patent: May 18, 2021

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Shoko Uetake, Tokyo (JP); Naoya Fukumoto, Tokyo (JP); Daisuke Yagyu, Tokyo (JP); Yuta Yamaguchi, Tokyo (JP); Naoko Ito, Tokyo (JP); Hiroyuki Tomita, Tokyo (JP); Ryuta Miyasaka, Tokyo (JP); Katsumi Murofushi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 515 days.

(21) Appl. No.: 15/640,729

(22) Filed: Jul. 3, 2017

(65) Prior Publication Data

US 2018/0009773 A1 Jan. 11, 2018

(30) Foreign Application Priority Data

Jul. 5, 2016 (JP) .............................. JP2016-133653

(51) Int. Cl.
*G11B 5/725* (2006.01)
*C10M 107/38* (2006.01)
(Continued)

(52) U.S. Cl.
CPC .......... *G11B 5/7257* (2020.08); *C07C 43/137* (2013.01); *C07C 43/23* (2013.01); *C10M 105/54* (2013.01); *C10M 107/38* (2013.01); *G11B 5/725* (2013.01); *C07D 303/28* (2013.01); *C10M 2211/0425* (2013.01);
(Continued)

(58) Field of Classification Search
CPC .............. C10M 107/38; C10M 105/54; C10M 2211/0425; G11B 5/725; G11B 5/7257; C20M 2213/00; C20M 2213/04; C20M 2213/043; C20M 2213/06; C20M 2213/0606; C10N 2040/18; C10N 2040/204; C10N 2050/023;
(Continued)

(56) References Cited

U.S. PATENT DOCUMENTS

2013/0209837 A1* 8/2013 Sagata ................... G11B 5/725
428/833
2015/0371672 A1* 12/2015 Sagata ................... C07C 43/23
428/833

FOREIGN PATENT DOCUMENTS

JP 2010-143855 A 7/2010
JP 2012-009090 A 1/2012
(Continued)

OTHER PUBLICATIONS

Notice of Reasons for Rejection dated Dec. 24, 2019, from the Japanese Patent Office in Application No. 2016-133653.

*Primary Examiner* — Holly Rickman
(74) *Attorney, Agent, or Firm* — Sughrue Mion, PLLC

(57) ABSTRACT

This fluorine-containing ether compound is represented by Formula (1).

$$R^1—R^2—CH_2—R^3—CH_2—R^4—R^5 \quad (1)$$

(in Formula (1), $R^1$ is an aryl group or an aralkyl group, $R^2$ is a divalent linking group having 0 or 1 polar group, $R^3$ is a perfluoropolyether chain, $R^4$ is a divalent linking group having 2 or 3 polar groups, and $R^5$ is an aryl group or an aralkyl group.)

12 Claims, 1 Drawing Sheet

(51) Int. Cl.
  *C07C 43/13* (2006.01)
  *C07C 43/23* (2006.01)
  *C10M 105/54* (2006.01)
  *C10N 30/06* (2006.01)
  *C10N 40/18* (2006.01)
  *C10N 50/00* (2006.01)
  *C07D 303/28* (2006.01)

(52) U.S. Cl.
  CPC ... *C10M 2213/043* (2013.01); *C10N 2030/06* (2013.01); *C10N 2040/18* (2013.01); *C10N 2050/023* (2020.05)

(58) Field of Classification Search
  CPC .............. C10N 2030/06; C08G 65/007; C08G 2650/48; C09D 171/00; C09D 171/02; C07D 303/28
  See application file for complete search history.

(56) References Cited

FOREIGN PATENT DOCUMENTS

| | | |
|---|---|---|
| JP | 2013-163667 A | 8/2013 |
| WO | 2009/123043 A1 | 10/2009 |
| WO | 2011/099131 A1 | 8/2011 |
| WO | 2015/087615 A1 | 6/2015 |

\* cited by examiner

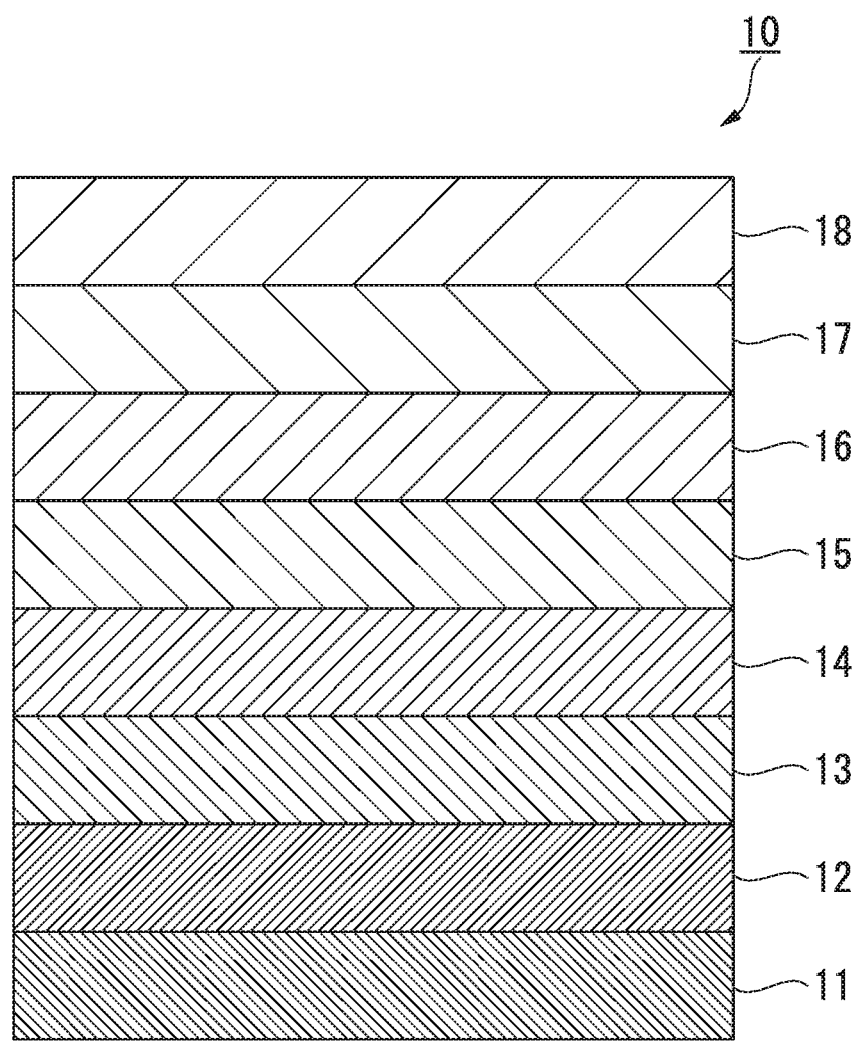

FLUORINE-CONTAINING ETHER COMPOUND, LUBRICANT FOR MAGNETIC RECORDING MEDIUM, AND MAGNETIC RECORDING MEDIUM

BACKGROUND OF THE INVENTION

Field of the Invention

The present invention relates to a fluorine-containing ether compound suitable for application as a lubricant of a magnetic recording medium, a lubricant for a magnetic recording medium including the same, and a magnetic recording medium.

This application claims priority to Japanese Patent Application No. 2016-133653 filed on Jul. 5, 2016, the contents of which are incorporated herein by reference.

Description of Related Art

In order to improve the recording density of magnetic recording/reproducing apparatuses, magnetic recording media suitable for high recording densities are being developed.

In the related art, there is a magnetic recording medium in which a recording layer is formed on a substrate and a protective layer of carbon or the like is formed on the recording layer. The protective layer protects the information recorded on the recording layer and improves the sliding of the magnetic head. However, it is not possible to sufficiently obtain durability of the magnetic recording medium simply by providing a protective layer on the recording layer. For this reason, in general, a lubricant is applied to the surface of the protective layer to form a lubricating layer.

As a lubricant used for forming a lubricating layer of a magnetic recording medium, for example, a lubricant was proposed containing a compound having a polar group such as a hydroxyl group at the end of a fluorine-based polymer having a repeating structure containing $CF_2$ (for example, refer to Patent Documents 1 and 2). In addition, a compound was proposed having a symmetrical structure having a substituted benzene at both ends of a perfluoropolyether main chain (for example, refer to Patent Document 3).

PRIOR ART DOCUMENT

Patent Document

[Patent Document 1] Japanese Unexamined Patent Application, First Publication No. 2013-163667
[Patent Document 2] Japanese Unexamined Patent Application, First Publication No. 2012-9090
[Patent Document 3] PCT International Publication No. WO2015/087615

SUMMARY OF THE INVENTION

In the magnetic recording/reproducing apparatuses, there is a demand to further reduce the floating height of the magnetic head. For this reason, it is required to further reduce the thickness of the lubricating layer in the magnetic recording medium.

When the thickness of the lubricating layer of the magnetic recording medium is reduced, pick-up in which components in the lubricating layer adhere to the magnetic head is suppressed. However, when the thickness of the lubricating layer is reduced, the wear resistance of the magnetic recording medium is insufficient, and the magnetic recording medium tends to deteriorate due to friction and wear by the magnetic head.

The present invention has been made in view of the above circumstances, and it is an object of the present invention to provide a fluorine-containing ether compound which is suitable for use as a material for a lubricant for a magnetic recording medium capable of forming a lubricating layer which is capable of suppressing pick-up and which obtains excellent wear resistance even when the thickness is reduced.

In addition, another object of the present invention is to provide a lubricant for a magnetic recording medium including the fluorine-containing ether compound of the present invention.

In addition, another object of the present invention is to provide a magnetic recording medium having a lubricating layer including the fluorine-containing ether compound of the present invention.

Means for Solving the Problem

The present inventors conducted intensive research to solve the problems described above.

As a result, it was found that it is sufficient to have a fluorine-containing ether compound in which an aryl group or an aralkyl group is arranged at one end of the perfluoropolyether chain via a divalent linking group having 0 or 1 polar group, and an aryl group or an aralkyl group is arranged at the other end of the perfluoropolyether chain via a divalent linking group having 2 or 3 polar groups, thereby completing the present invention.

That is, the present invention relates to the following aspects.

[1] A fluorine-containing ether compound according to an aspect of the present invention is represented by Formula (1).

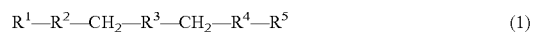

(In Formula (1), $R^1$ is an aryl group or an aralkyl group, $R^2$ is a divalent linking group having 0 or 1 polar group, $R^3$ is a perfluoropolyether chain, $R^4$ is a divalent linking group having 2 or 3 polar groups, and $R^5$ is an aryl group or an aralkyl group.)

[2] In the fluorine-containing ether compound according to [1], at least one of the polar groups in the polar groups included in $R^2$ and $R^4$ of Formula (1) may be a hydroxyl group.

[3] In the fluorine-containing ether compound according to [1] or [2], the polar groups included in $R^2$ and $R^4$ of Formula (1) may all be hydroxyl groups.

[4] In the fluorine-containing ether compound according to any one of [1] to [3], $R^4$ in Formula (1) may be represented by Formula (2).

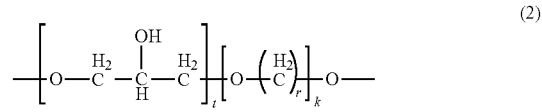

(In Formula (2), t represents an integer of 2 or 3, r represents an integer of 1 to 4, and k represents an integer of 0 to 3.)

[5] In the fluorine-containing ether compound according to any one of [1] to [4], $R^3$ in Formula (1) may be represented by any one of Formulas (3-1), (3-2), and (3-3).

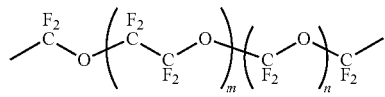

(3-1)

(In Formula (3-1), m represents an integer of 1 to 30, and n represents an integer of 0 to 30.)

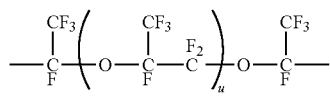

(3-2)

(In Formula (3-2), u represents an integer of 1 to 30.)

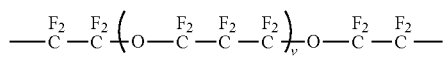

(3-3)

(In Formula (3-3), v represents an integer of 1 to 30.)

[6] In the fluorine-containing ether compound according to any one of [1] to [5], $R^1$ in Formula (1) may be any one selected from a benzene ring group which may have a substituent, a naphthalene ring group which may have a substituent, a benzyl group which may have a substituent, or a naphthylmethyl group which may have a substituent.

[7] In the fluorine-containing ether compound according to any one of [1] to [6], $R^2$ in Formula (1) may be represented by —O— or Formula (4).

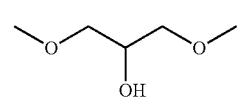

(4)

[8] In the fluorine-containing ether compound according to any one of [1] to [7], $R^4$ in Formula (1) may have —(O—CH$_2$—CH$_2$)$_z$—O— (z in the formula represents an integer of 1 to 3) at an end on the $R^5$ side.

[9] In the fluorine-containing ether compound according to any one of [1] to [8], $R^5$ in Formula (1) may be any one selected from a benzene ring group which may have a substituent, a naphthalene ring group which may have a substituent, a benzyl group which may have a substituent, or a naphthylmethyl group which may have a substituent.

[10] In the fluorine-containing ether compound according to any one of [1] to [9], the compound in Formula (1) may be represented by Formula (5).

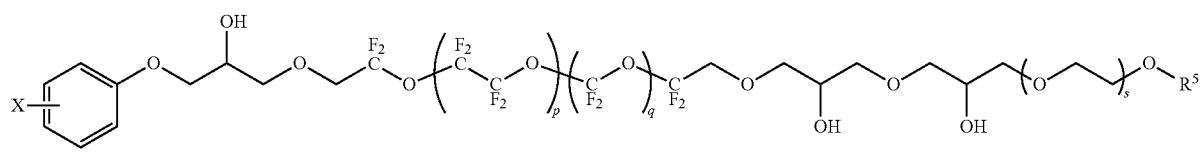

(5)

(In Formula (5), X represents any one of a hydrogen atom, a halogen atom, an alkyl group having 1 to 5 carbon atoms, an alkoxy group having 1 to 5 carbon atoms, and a fluoroalkyl group having 1 to 5 carbon atoms, and may be one or a plurality and, when a plurality, X may be the same or different from each other. $R^5$ represents an aryl group or an aralkyl group, p represents an integer of 1 to 30, q represents an integer of 0 to 30, and s represents an integer of 0 to 3.)

[11] In the fluorine-containing ether compound according to any one of [1] to [9], the compound in Formula (1) may be represented by Formula (6).

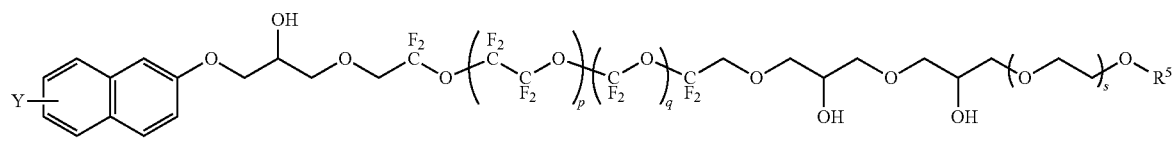

(6)

(In Formula (6), Y represents any one of a hydrogen atom, a halogen atom, an alkyl group having 1 to 5 carbon atoms, an alkoxy group having 1 to 5 carbon atoms, and a fluoroalkyl group having 1 to 5 carbon atoms, and may be one or a plurality and, when a plurality, Y may be the same or different from each other, $R^5$ represents an aryl group or an aralkyl group, p represents an integer of 1 to 30, q represents an integer of 0 to 30, and s represents an integer of 0 to 3.)

[12] In the fluorine-containing ether compound according to any one of [1] to [9], the compound in Formula (1) may be represented by Formula (7).

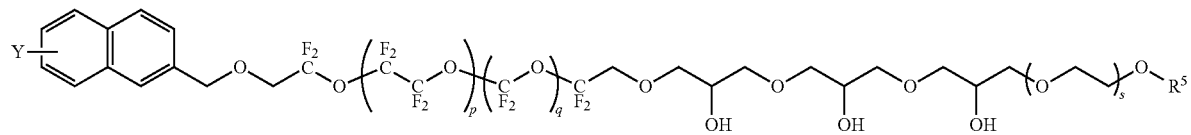

(7)

(In Formula (7), Y represents any one of a hydrogen atom, a halogen atom, an alkyl group having 1 to 5 carbon atoms, an alkoxy group having 1 to 5 carbon atoms, and a fluoroalkyl group having 1 to 5 carbon atoms, and may be one or a plurality and, when a plurality, Y may be the same or different from each other, $R^5$ represents an aryl group or an aralkyl group, p represents an integer of 1 to 30, q represents an integer of 0 to 30, and s represents an integer of 0 to 3.)

[13] In the fluorine-containing ether compound according to any one of [1] to [12], a number-average molecular weight may be in a range of 500 to 10,000.

[14] A lubricant for a magnetic recording medium according to another aspect of the present invention includes the fluorine-containing ether compound according to any one of [1] to [13].

[15] A magnetic recording medium according to still another aspect of the present invention includes at least a magnetic layer; a protective layer; and a lubricating layer sequentially provided on a substrate, in which the lubricating layer includes the fluorine-containing ether compound according to any one of [1] to [13].

[16] In the magnetic recording medium according to [15], an average film thickness of the lubricating layer may be 0.5 nm to 2 nm.

Effect of the Invention

The fluorine-containing ether compound of the present invention is a compound represented by Formula (1) and is suitable as a material for a lubricant for a magnetic recording medium.

Since the lubricant for a magnetic recording medium of the present invention includes the fluorine-containing ether compound of the present invention, it is possible to form a lubricating layer having excellent wear resistance and capable of suppressing pick-up even when the thickness is reduced.

Since the magnetic recording medium of the present invention has a lubricating layer having excellent wear resistance and capable of suppressing pick-up, the durability is excellent.

BRIEF DESCRIPTION OF THE DRAWINGS

FIG. 1 is a schematic cross-sectional view showing one embodiment of a magnetic recording medium of the present invention.

DETAILED DESCRIPTION OF THE INVENTION

A detailed description will be given below of the fluorine-containing ether compound, the lubricant for a magnetic recording medium, and the magnetic recording medium of the present invention.

Here, the present invention is not limited to only the embodiments described below.

[Fluorine-Containing Ether Compound]

The fluorine-containing ether compound of the present embodiment is represented by Formula (1).

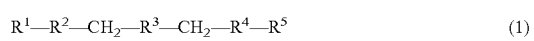

(In Formula (1), $R^1$ is an aryl group or an aralkyl group, $R^2$ is a divalent linking group having 0 or 1 polar group, $R^3$ is a perfluoropolyether chain, $R^4$ is a divalent linking group having 2 or 3 polar groups, and $R^5$ is an aryl group or an aralkyl group.)

Here, description will be given of the reasons why the wear resistance is excellent and it is possible to suppress pick-up even when the thickness is reduced in a case where a lubricating layer is formed on the protective layer of the magnetic recording medium using a lubricant for a magnetic recording medium including the fluorine-containing ether compound of the present embodiment (may be abbreviated below as "lubricant").

As shown in Formula (1), in the fluorine-containing ether compound of the present embodiment, an aryl group or an aralkyl group represented by $R^1$ is arranged via a divalent linking group having 0 or 1 polar group represented by $R^2$ at one end of a perfluoropolyether chain (may be abbreviated below as "PFPE chain"), represented by $R^3$. In the lubricating layer including the fluorine-containing ether compound of the present embodiment, the PFPE chain covers the surface of the protective layer and reduces the frictional force between the magnetic head and the protective layer. In addition, the aryl group or the aralkyl group represented by $R^1$ improves the wear resistance of the lubricating layer including the fluorine-containing ether compound of the present embodiment due to the intermolecular interaction of the aromatic rings. Therefore, the lubricating layer including the fluorine-containing ether compound of the present embodiment obtains excellent wear resistance in comparison with a lubricating layer including a fluorine-containing ether compound in which, for example, a hydroxyl group is arranged instead of the aryl group or the aralkyl group represented by $R^1$.

In addition, an aryl group or an aralkyl group represented by $R^5$ is arranged via a divalent linking group having 2 or 3 polar groups represented by $R^4$ at the end (the other end) of the PFPE chain represented by $R^3$ in Formula (1) opposite to $R^2$. Two or three polar groups included in the divalent linking group represented by $R^4$ and the aryl group or aralkyl group represented by $R^5$ bring the fluorine-containing ether compound and the protective layer into tight contact with each other in the lubricating layer including the fluorine-containing ether compound of the present embodiment to suppress pick-up.

It is considered that this is due to the bond between the protective layer and two or three polar groups of $R^4$ linked to the PFPE chain and the intermolecular interaction between the aromatic ring included in $R^5$ and the protective film. That is, the groups represented by $R^4$ and $R^5$ contribute to the adhesion between the protective layer coated with the lubricant including the fluorine-containing ether compound of the present embodiment and the lubricating layer formed by coating the lubricant. Therefore, in the lubricating layer including the fluorine-containing ether compound of the present embodiment, it is possible to prevent the fluorine-containing ether compound which is present without being adhered to the protective layer from aggregating and adhering to the magnetic head as foreign matter (smear), and pick-up is suppressed.

It is possible to appropriately select $R^4$ and $R^5$ in Formula (1) according to the performance or the like required for the lubricant including a fluorine-containing ether compound.

Examples of the polar group included in $R^4$ include a hydroxyl group, a carboxyl group, an amino group, and the like. For the reason that the adhesion between the protective layer and the lubricating layer including the fluorine-containing ether compound is improved, it is preferable that at least one of the polar groups out of the polar groups included in $R^4$ be a hydroxyl group. Here, the ether bond (—O—) is not included in the polar group in $R^4$. The two or three polar groups included in the divalent linking group represented by $R^4$ may all be different from each other, may all be the same, or may be partially the same. In the present embodiment, it is preferable that all of the two or three polar groups included in the divalent linking group represented by $R^4$ be hydroxyl groups. When all of the two or three polar groups described above are hydroxyl groups, in particular, in a case where the protective layer to be coated with the lubricant is formed of carbon or carbon including nitrogen, the fluorine-containing ether compound is capable of forming a lubricating layer with a better adhesion to the protective layer.

In addition, it is preferable that $R^4$ in Formula (1) have an ethylene oxide structure represented by —(O—CH$_2$—CH$_2$)$_z$—O— (in the formula, z represents an integer of 1 to 3) at the end on the $R^5$ side. In this case, the distance between two or three polar groups included in $R^4$ and the aryl group or aralkyl group represented by $R^5$ does not become excessively long. Therefore, the adhesion between the lubricating layer formed by coating the lubricant including the fluorine-containing ether compound and the protective layer is good.

$R^5$ in Formula (1) is an aryl group or an aralkyl group. Examples of the aryl group represented by $R^5$ include a benzene ring group, a naphthalene ring group, an anthracene ring group, a heterocyclic group, and the like. These aryl groups may be substituted with a substituent such as a halogen or a substituent having 1 to 5 carbon atoms. Examples of the substituent having 1 to 5 carbon atoms include an alkyl group, an alkoxy group, a fluoroalkyl group, and the like.

The alkylene group of the aralkyl group represented by $R^5$ is preferably a methylene group or an ethylene group.

As the aryl group or the aralkyl group represented by $R^5$, any one selected from a benzene ring group which may have a substituent, a naphthalene ring group which may have a substituent, a benzyl group which may have a substituent, or a naphthylmethyl group which may have a substituent is preferable since the interaction with the substrate is appropriate. Specific examples of $R^5$ include a methoxyphenyl group, a naphthyl group, a methoxybenzyl group, a naphthylmethyl group, a methoxynaphthyl group, a thiophene group, a thiophenemethyl group, a quinoline group, a 3,5-bistrifluoromethylphenyl group, and the like.

$R^4$ in Formula (1) is preferably a linking group represented by Formula (2). $R^4$ represented by Formula (2) contributes to the adhesion between the protective layer coated with the lubricant including the fluorine-containing ether compound of the present embodiment and the lubricating layer formed by coating the lubricant.

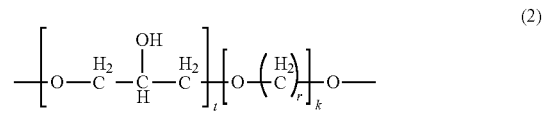

(In Formula (2), t represents an integer of 2 or 3, r represents an integer of 1 to 4, and k represents an integer of 0 to 3.)

In Formula (2), t is an integer of 2 or 3. In a case where t is an integer of 2 or 3, the divalent linking group represented by $R^4$ has two or three hydroxyl groups. When t in Formula (2) is an integer of 2 or 3, the adhesion between the lubricating layer including the fluorine-containing ether compound and the protective layer is further improved, and it is possible to effectively suppress pick-up.

In Formula (2), k is an integer of 0 to 3, preferably 0 or 1. When k is 0 or 1, the distance between two or three hydroxyl groups included in $R^4$ and the aryl group or aralkyl group represented by $R^5$ is appropriate. Therefore, the adhesion between the lubricating layer formed by coating the lubricant including the fluorine-containing ether compound and the protective layer is improved.

In Formula (2), r is an integer of 1 to 4, preferably 2. When r is 2, the distance between two or three hydroxyl groups included in $R^4$ and the aryl group or aralkyl group represented by $R^5$ is appropriate.

In Formula (1), $R^3$ is a perfluoropolyether chain (PFPE chain). In the case where a lubricant including a fluorine-containing ether compound is coated on the protective layer to form a lubricating layer, the PFPE chain covers the surface of the protective layer and imparts lubricity to the lubricating layer to reduce the frictional force between the magnetic head and the protective layer.

$R^3$ is not particularly limited and it is possible to appropriately select $R^3$ according to the performance required for the lubricant including a fluorine-containing ether compound.

$R^3$ in Formula (1) is preferably a PFPE chain represented by Formula (3-1) since it is easy to synthesize a fluorine-containing ether compound.

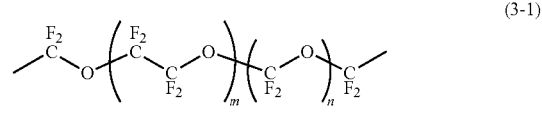

(In Formula (3-1), m represents an integer of 1 to 30, and n represents an integer of 0 to 30.)

In Formula (3-1), the order of arrangement of (CF$_2$—CF$_2$—O) and (CF$_2$—O), which are repeating units. is not particularly limited. The number m of (CF$_2$—CF$_2$—O) and the number n of (CF$_2$—O) in Formula (3-1) may be the same or may be different. Formula (3-1) may include any one of a random copolymer, a block copolymer, and an alternating copolymer formed of the monomer units (CF$_2$—CF$_2$—O) and (CF$_2$—O).

In a case where $R^3$ in Formula (1) is Formula (3-1), m is an integer of 1 to 30, preferably an integer of 1 to 20, and more preferably an integer of 1 to 15. In Formula (1), in a case where $R^3$ is Formula (3-1), n is an integer of 0 to 30, preferably an integer of 0 to 20, and more preferably an integer of 0 to 15. In addition, in a case where n is 0, m is preferably an integer of 1 to 17.

In Formula (1), $R^3$ may be Formula (3-2) or Formula (3-3).

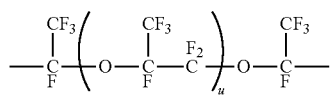
(3-2)

(In Formula (3-2), u represents an integer of 1 to 30.)

In Formula (3-2), in a case where u is an integer of 1 to 30, the number-average molecular weight of the fluorine-containing ether compound of the present embodiment tends to be in a preferable range. u is preferably an integer of 3 to 20, and more preferably an integer of 4 to 10.

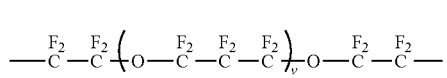
(3-3)

(In Formula (3-3), v represents an integer of 1 to 30.)

In Formula (3-3), in a case where v is an integer of 1 to 30, the number-average molecular weight of the fluorine-containing ether compound of the present embodiment tends to be in a preferable range. v is preferably an integer of 3 to 20, and more preferably an integer of 4 to 10.

In a case where $R^3$ in Formula (1) is any one of Formulas (3-1) to (3-3), synthesis of the fluorine-containing ether compound is easy, which is preferable. In addition, in the case where $R^3$ in Formula (1) is any one of Formulas (3-1) to (3-3), the ratio of the number of oxygen atoms (ether bond (—O—) number) with respect to the number of carbon atoms in the perfluoropolyether chain is appropriate. For this reason, a fluorine-containing ether compound having appropriate hardness is obtained. Thus, the fluorine-containing ether compound coated on the protective layer does not easily aggregate on the protective layer, and it is possible to form a lubricating layer having a reduced thickness with a sufficient coverage ratio. In addition, in a case where $R^3$ in Formula (1) is Formula (3-1), the raw materials are easily obtained, which is more preferable.

$R^1$ in Formula (1) is an aryl group or an aralkyl group. Examples of the aryl group represented by $R^1$ include a benzene ring group, a naphthalene ring group, an anthracene ring group, a heterocyclic group, and the like. These aryl groups may be substituted with a substituent such as a halogen or a substituent having 1 to 5 carbon atoms. Examples of the substituent having 1 to 5 carbon atoms include an alkyl group, an alkoxy group, a fluoroalkyl group, and the like.

The alkylene group of the aralkyl group represented by $R^1$ is preferably a methylene group or an ethylene group.

The aryl group or the aralkyl group represented by $R^1$ is preferably any one selected from a benzene ring group which may have a substituent, a naphthalene ring group which may have a substituent, a benzyl group which may have a substituent, or a naphthylmethyl group which may have a substituent since an intermolecular interaction occurs. Specifically, examples of the aryl group represented by $R^1$ include a methoxyphenyl group, a naphthyl group, a methoxynaphthyl group, a quinoline group, a thiophene group, and the like. Examples of the aralkyl group represented by $R^1$ include a methoxybenzyl group, a naphthylmethyl group, a thiophenemethyl group, and the like.

In the case where the aryl group or the aralkyl group represented by $R^1$ is a phenyl group which may have a substituent, a naphthyl group which may have a substituent, or an arylmethyl group, the intermolecular interaction of the aromatic ring is suitable, which is more preferable.

In the fluorine-containing ether compound of the present embodiment, $R^1$ in Formula (1) and $R^5$ in Formula (1) may be the same or may be different.

$R^2$ in Formula (1) is a divalent linking group having 0 or one polar group. It is possible to appropriately select the divalent linking group represented by $R^2$ according to the performance required for the lubricant including a fluorine-containing ether compound.

The divalent linking group represented by $R^2$ preferably has one polar group. In this case, in the lubricating layer including the fluorine-containing ether compound, the distance between the fluorine-containing ether compounds becomes appropriate due to the intermolecular interaction of the fluorine-containing ether compound, and the wear resistance of the lubricating layer is favorable. Examples of the polar group included in the linking group include a hydroxyl group, a carboxyl group, an amino group, an aminocarboxyl group, and the like, and a hydroxyl group is preferable. When the divalent linking group represented by $R^2$ includes one hydroxyl group, in particular, in a case where the protective layer to be coated with a lubricant is formed of carbon or carbon including nitrogen, the distance between the fluorine-containing ether compounds in the lubricant coated on the protective layer is more appropriate, and the wear resistance of the lubricating layer is further improved.

In Formula (1), the divalent linking group represented by $R^2$ preferably has 1 to 20 carbon atoms. When the number of carbon atoms is 20 or less, it is possible to prevent the number-average molecular weight of the fluorine-containing ether compound from becoming excessively large. The number of carbon atoms of the divalent linking group represented by $R^2$ is more preferably 3 to 12.

Specifically, $R^2$ in Formula (1) is preferably —O— or represented by Formula (4).

In a case where $R^2$ in Formula (1) is —O—, when t of $R^4$ in Formula (2) is 3, the adhesion between the protective layer and the lubricating layer is better, which is preferable.

In a case where $R^2$ in Formula (1) is represented by Formula (4), the divalent linking group represented by $R^2$ has one hydroxyl group. In this case, in the lubricating layer including the fluorine-containing ether compound, the distance between the fluorine-containing ether compounds is more appropriate due to the intermolecular interaction of the fluorine-containing ether compound, and the wear resistance of the lubricating layer is better.

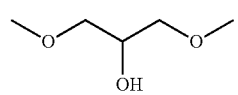
(4)

The fluorine-containing ether compound of the present embodiment is preferably any one of compounds represented by Formulas (5) to (7).

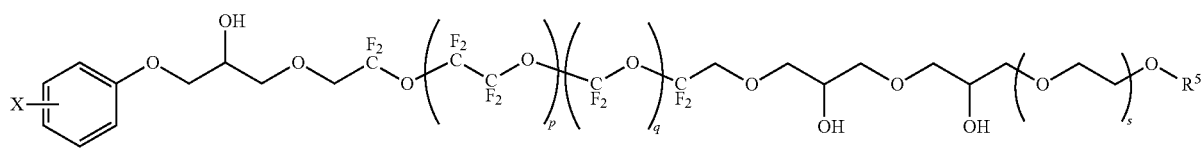

(5)

(In Formula (5), X represents any one of a hydrogen atom, a halogen atom, an alkyl group having 1 to 5 carbon atoms, an alkoxy group having 1 to 5 carbon atoms, and a fluoroalkyl group having 1 to 5 carbon atoms, and may be one or a plurality, and when a plurality, X may be the same or different from each other. $R^5$ represents an aryl group or an aralkyl group, p represents an integer of 1 to 30, q represents an integer of 0 to 30, and s represents an integer of 0 to 3.)

an alkoxy group having 1 to 5 carbon atoms, and a fluoroalkyl group having 1 to 5 carbon atoms, the intermolecular interaction of the aromatic ring is suitable, which is more preferable. Here, X may be one or plural, and when plural, X's may be the same as or different from each other.

Y in Formula (6) or Formula (7) is any one of a hydrogen atom, a halogen atom, an alkyl group having 1 to 5 carbon atoms, an alkoxy group having 1 to 5 carbon atoms, and a

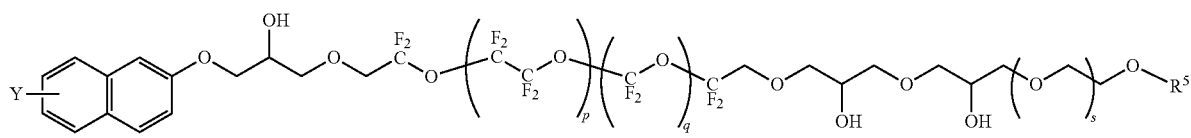

(6)

(In Formula (6), Y represents any one of a hydrogen atom, a halogen atom, an alkyl group having 1 to 5 carbon atoms, an alkoxy group having 1 to 5 carbon atoms, and a fluoroalkyl group having 1 to 5 carbon atoms, and may be one or a plurality, and when a plurality, Y may be the same or different from each other. $R^5$ represents an aryl group or an aralkyl group, p represents an integer of 1 to 30, q represents an integer of 0 to 30, and s represents an integer of 0 to 3.)

fluoroalkyl group having 1 to 5 carbon atoms. In a case where Y is any one of a hydrogen atom, an alkyl group having 1 to 5 carbon atoms, an alkoxy group having 1 to 5 carbon atoms, and a fluoroalkyl group having 1 to 5 carbon atoms, the intermolecular interaction of the aromatic ring is suitable, which is more preferable. Here, Y may be one or plural, and when plural, Y's may be the same as or different from each other.

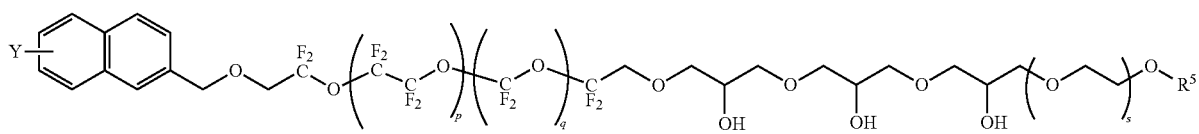

(7)

(In Formula (7), Y represents any one of a hydrogen atom, a halogen atom, an alkyl group having 1 to 5 carbon atoms, an alkoxy group having 1 to 5 carbon atoms, and a fluoroalkyl group having 1 to 5 carbon atoms, and may be one or a plurality, and when a plurality, Y may be the same or different from each other. $R^5$ represents an aryl group or an aralkyl group, p represents an integer of 1 to 30, q represents an integer of 0 to 30, and s represents an integer of 0 to 3.)

X in Formula (5) is any one of a hydrogen atom, a halogen atom, an alkyl group having 1 to 5 carbon atoms, an alkoxy group having 1 to 5 carbon atoms, and a fluoroalkyl group having 1 to 5 carbon atoms. In a case where X is any one of a hydrogen atom, an alkyl group having 1 to 5 carbon atoms, $R^5$ in Formulas (5) to (7) is an aryl group or an aralkyl group. $R^5$ in Formulas (5) to (7) is the same as $R^5$ in Formula (1).

p in Formulas (5) to (7) is an integer of 1 to 30 and is the same as m in Formula (3-1). In addition, q in Formulas (5) to (7) is an integer of 1 to 30 and is the same as n in Formula (3-1).

In Formulas (5) to (7), s is an integer of 0 to 3, preferably 0 or 1. When s is 0 or 1, the distance between $R^5$ in Formulas (5) to (7) and the hydroxyl group closest to $R^5$ is appropriate.

Specifically, the fluorine-containing ether compound of the present embodiment is preferably any one of compounds represented by Formulas (8) to (11).

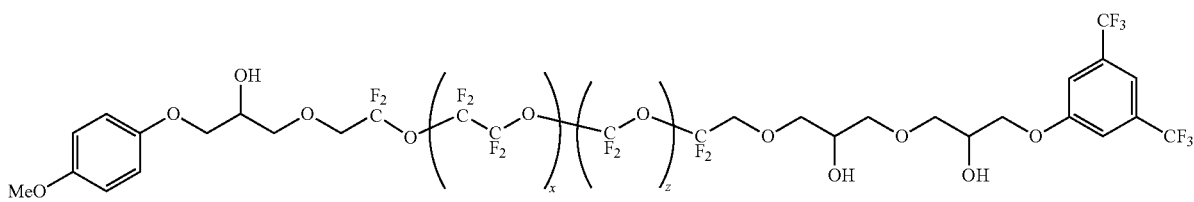

(8)

(In Formula (8), x represents an integer of 1 to 15, z represents an integer of 0 to 15, and Me represents a methyl group.)

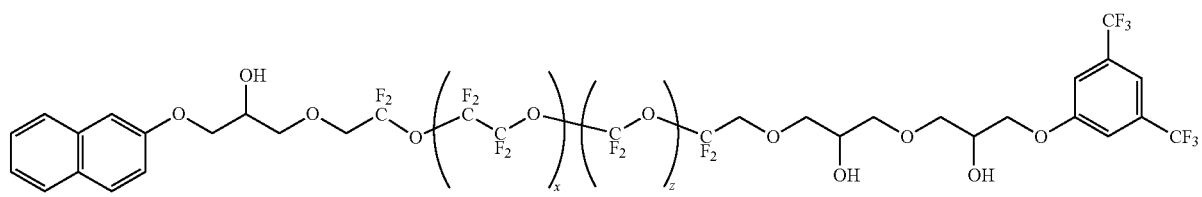

(9)

(In Formula (9), x represents an integer of 1 to 15, and z represents an integer of 0 to 15.)

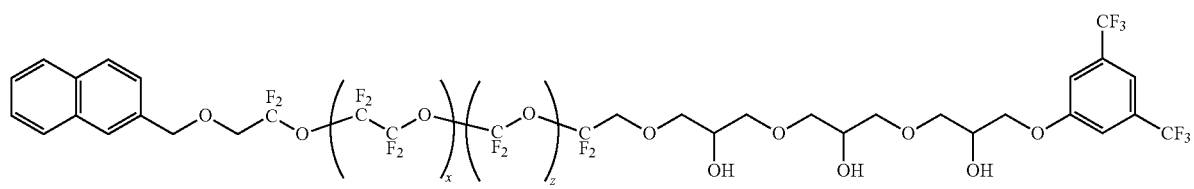

(10)

(In Formula (10), x represents an integer of 1 to 15, and z represents an integer of 0 to 15.)

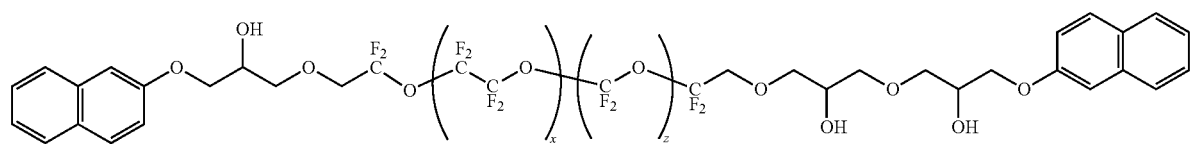

(11)

(In Formula (11), x represents an integer of 1 to 15, and z represents an integer of 0 to 15.)

In a case where the compound represented by Formula (1) is any one of the compounds represented by Formulas (8) to (11), raw materials are easily available, which are preferable. In addition, any one of the compounds represented by Formulas (8) to (11) is excellent in wear resistance and it is possible to form a lubricating layer capable of suppressing pick-up, which is preferable.

The fluorine-containing ether compound of the present embodiment preferably has a number-average molecular weight in a range of 500 to 10,000. When the number-average molecular weight is 500 or more, the lubricant including the fluorine-containing ether compound of the present embodiment does not easily evaporate and it is possible to prevent the lubricant from evaporating and transferring to the magnetic head. The number-average molecular weight of the fluorine-containing ether compound is more preferably 1,500 or more. In addition, when the number-average molecular weight is 10,000 or less, the viscosity of the fluorine-containing ether compound is appropriate, and it is possible to easily form a thin lubricating layer by coating a lubricant including the fluorine-containing ether compound. The number-average molecular weight of the fluorine-containing ether compound is preferably 3,000 or less since the viscosity is easily handled when applied to a lubricant.

The number-average molecular weight is a value measured by $^1$H-NMR and $^{19}$F-NMR by AVANCE III 400 manufactured by Bruker BioSpin K.K. In the measurement of nuclear magnetic resonance (NMR), the sample was diluted in a hexafluorobenzene/d-acetone (¼ v/v) solvent and used for measurement. Based on the $^{19}$F-NMR chemical shift, the peak of hexafluorobenzene was −164.7 ppm, and based on the $^1$H-NMR chemical shift, the peak of acetone was 2.2 ppm.

[Manufacturing Method]

The method for manufacturing the fluorine-containing ether compound of the present embodiment is not particularly limited, and manufacturing is possible using a manufacturing method known in the related art. It is possible to manufacture the fluorine-containing ether compound of the present embodiment, for example, by using the manufacturing method described below.

First, a fluorine compound having hydroxymethyl groups (—CH$_2$OH) arranged at both ends of a perfluoropolyether chain corresponding to R$^3$ in Formula (1) is prepared.

Subsequently, the hydroxyl group of the hydroxymethyl group arranged at one end of the fluorine compound is substituted with an end group formed of R$^1$—R$^2$— in Formula (1) (first reaction). Thereafter, the hydroxyl group of the hydroxymethyl group arranged at the other end is substituted with an end group formed of —R$^4$—R$^5$ in Formula (1) (second reaction).

It is possible to carry out the first reaction and the second reaction by a method known in the related art, and it is possible to appropriately determine the method according to the type of R$^1$, R$^2$, R$^4$, R$^5$ in Formula (1), and the like. In addition, either of the first reaction and the second reaction may be performed first.

By the above method, the compound represented by Formula (1) is obtained.

The fluorine-containing ether compound of the present embodiment is a compound represented by Formula (1). Accordingly, when a lubricating layer is formed on the protective layer using the lubricant including the fluorine-containing ether compound, the surface of the protective layer is covered with the PFPE chain represented by R$^3$ in Formula (1), and the frictional force between the magnetic head and the protective layer is reduced. In addition, in the lubricating layer formed using the lubricant including the fluorine-containing ether compound of the present embodiment, excellent wear resistance is obtained by the intermolecular interaction of the aromatic ring of the group represented by R$^1$. Therefore, the lubricant including the fluorine-containing ether compound of the present embodiment is able to form a lubricating layer having excellent wear resistance even when the thickness thereof is reduced.

In addition, in the fluorine-containing ether compound of the present embodiment, due to the bond between two or three polar groups of R$^4$, which are linked to the PFPE chain, and the protective layer and the bond between the aromatic ring, which is included in R$^5$, and the protective layer, the PFPE chain adheres on the protective layer. Therefore, in the lubricating layer formed using the lubricant including the fluorine-containing ether compound of the present embodiment, it is possible to prevent the fluorine-containing ether compound in the lubricating layer, which is present without being adhered (adsorbed) to the protective layer, from being adhered to the magnetic head as a foreign substance (smear) and pick-up is suppressed.

From these facts, the fluorine-containing ether compound of the present embodiment is suitable as a material for a lubricant for a magnetic recording medium.

[Lubricant for Magnetic Recording Medium]

The lubricant for a magnetic recording medium of the present embodiment includes a fluorine-containing ether compound represented by Formula (1).

As long as the lubricant of the present embodiment is in a range which does not impair characteristics due to the inclusion of the fluorine-containing ether compound represented by Formula (1), it is possible to use known materials for a lubricant in a mixture as necessary.

Specific examples of known materials include FOMBLIN (registered trademark) ZDIAC, FOMBLIN ZDOL, FOMBLIN AM-2001 (manufactured by Solvay Solexis Inc.), Moresco A 20 H (manufactured by Moresco Corp.), and the like.

A known material used by mixing with the lubricant of the present embodiment preferably has a number-average molecular weight of 1,000 to 10,000.

In the case where the lubricant of the present embodiment includes another material of the fluorine-containing ether compound represented by Formula (1), the content of the fluorine-containing ether compound represented by Formula (1) in the lubricant of the present embodiment is preferably 50% by mass or more, and more preferably 70% by mass or more.

Since the lubricant of the present embodiment includes the fluorine-containing ether compound represented by Formula (1), it is possible to form a lubricating layer having a reduced thickness and excellent wear resistance.

In addition, since the lubricant of the present embodiment includes the fluorine-containing ether compound represented by Formula (1), the adhesion to the protective layer is good. Therefore, in the lubricating layer formed using the lubricant of the present embodiment, the fluorine-containing ether compound present without being adhered (adsorbed) to the protective layer is prevented from adhering to the magnetic head as a foreign matter (smear), and pick-up is suppressed.

[Magnetic Recording Medium]

FIG. 1 is a schematic cross-sectional view showing one embodiment of the magnetic recording medium of the present invention.

The magnetic recording medium 10 of the present embodiment has a structure in which an adhesive layer 12, a soft magnetic layer 13, a first underlayer 14, a second underlayer 15, a magnetic layer 16, a protective layer 17, and a lubricating layer 18 are sequentially provided on a substrate 11.

[Substrate]

As the substrate 11, for example, it is possible to use a nonmagnetic substrate or the like in which a film formed of NiP or NiP alloy is formed on a substrate formed of a metal or an alloy material such as Al or an Al alloy.

In addition, as the substrate 11, a nonmagnetic substrate formed of a non-metallic material such as glass, ceramics, silicon, silicon carbide, carbon, resin, or the like may be used, or a nonmagnetic substrate in which a film of an NiP or NiP alloy is formed on a base formed of these non-metal materials may be used.

[Adhesive Layer]

The adhesive layer 12 prevents the progress of corrosion of the substrate 11 in a case where the substrate 11 and the soft magnetic layer 13 provided on the adhesive layer 12 are arranged in contact with each other.

It is possible to appropriately select the material of the adhesive layer 12 from, for example, Cr, a Cr alloy, Ti, a Ti alloy, and the like. It is possible to form the adhesive layer 12 by, for example, a sputtering method.

[Soft Magnetic Layer]

It is preferable that the soft magnetic layer 13 have a structure in which a first soft magnetic film, an intermediate layer formed of a Ru film, and a second soft magnetic film are laminated in order. That is, the soft magnetic layer 13 preferably has a structure in which, by interposing an intermediate layer formed of a Ru film between two layers of soft magnetic films, the upper and lower soft magnetic films of the intermediate layer are bonded by anti-ferro-coupling (AFC). When the soft magnetic layer 13 has an AFC-bonded structure, it is possible to increase the resistance to external magnetic fields and the resistance to the Wide Area Tack Erasure (WATE) phenomenon, which is a problem peculiar to perpendicular magnetic recording.

It is preferable that the first soft magnetic film and the second soft magnetic film be films formed of a CoFe alloy. In a case where the first soft magnetic film and the second soft magnetic film are films formed of a CoFe alloy, it is possible to realize a high saturation magnetic flux density Bs (1.4 (T) or more).

In addition, it is preferable to add any one of Zr, Ta, or Nb to the CoFe alloy used for the first soft magnetic film and the second soft magnetic film. Due to this, amorphization of the first soft magnetic film and the second soft magnetic film is promoted, and it is possible to improve the orientation of the first underlayer (seed layer), and it is also possible to reduce the floating height of the magnetic head.

It is possible to form the soft magnetic layer 13 by, for example, a sputtering method.

[First Underlayer]

The first underlayer 14 is a layer for controlling the orientation and crystal size of the second underlayer 15 and the magnetic layer 16 provided thereon. The first underlayer 14 is provided to increase the components in the direction perpendicular to the substrate surface of the magnetic flux generated from the magnetic head and fix the magnetization direction of the magnetic layer 16 more firmly in the direction perpendicular to the substrate 11.

The first underlayer 14 is preferably a layer formed of a NiW alloy. In the case where the first underlayer 14 is a layer formed of a NiW alloy, other elements such as B, Mn, Ru, Pt, Mo, Ta and the like may be added to the NiW alloy as necessary.

It is possible to form the first underlayer 14 by, for example, a sputtering method.

[Second Underlayer]

The second underlayer 15 is a layer which controls the orientation of the magnetic layer 16 so as to be favorable. The second underlayer 15 is preferably a layer formed of Ru or a Ru alloy.

The second underlayer 15 may be a layer formed of one layer or a plurality of layers. In the case where the second underlayer 15 is formed of a plurality of layers, all of the layers may be formed of the same material, or at least one layer may be formed of a different material.

It is possible to form the second underlayer 15 by, for example, a sputtering method.

[Magnetic Layer]

The magnetic layer 16 is formed of a magnetic film in which the axis of easy magnetization is perpendicular or horizontal to the substrate surface. The magnetic layer 16 is a layer including Co and Pt and may be a layer including an oxide or Cr, B, Cu, Ta, Zr or the like in order to further improve the SNR characteristics.

Examples of the oxide contained in the magnetic layer 16 include $SiO_2$, SiO, $Cr_2O_3$, CoO, $Ta_2O_3$, $TiO_2$, and the like.

The magnetic layer 16 may be formed of one layer or formed of a plurality of magnetic layers formed of materials having different compositions.

For example, in the case where the magnetic layer 16 is formed of three layers of a first magnetic layer, a second magnetic layer, and a third magnetic layer, the first magnetic layer includes Co, Cr, and Pt, and preferably has a granular structure formed of a material including an oxide. As the oxide contained in the first magnetic layer, for example, it is preferable to use oxides such as Cr, Si, Ta, Al, Ti, Mg, and Co. Among these, in particular, it is possible to suitably use $TiO_2$, $CR_2O_3$, $SiO_2$, and the like. In addition, the first magnetic layer is preferably formed of a composite oxide to which two or more oxides are added. Among these, it is possible to preferably use $Cr_2O_3$—$SiO_2$, $Cr_2O_3$—$TiO_2$, $SiO_2$—$TiO_2$, and the like.

In addition to Co, Cr, Pt and an oxide, the first magnetic layer is able to include one or more elements selected from B, Ta, Mo, Cu, Nd, W, Nb, Sm, Tb, Ru, and Re. By including one or more of the above elements, it is possible to promote miniaturization of the magnetic particles, to improve crystallinity and orientation, and to obtain recording/reproduction characteristics and thermal fluctuation characteristics suitable for higher density recording.

For the second magnetic layer, it is possible to use the same material as the first magnetic layer. It is preferable that the second magnetic layer have a granular structure.

The third magnetic layer preferably has a non-granular structure formed of a material which includes Co, Cr, and Pt and which does not include oxide. In addition to Co, Cr, and Pt, it is possible for the third magnetic layer to include one or more elements selected from B, Ta, Mo, Cu, Nd, W, Nb, Sm, Tb, Ru, Re, and Mn. Including the above elements in addition to Co, Cr and Pt in the third magnetic layer makes it possible to promote miniaturization of the magnetic particles, to improve crystallinity and orientation, and to obtain recording and reproduction characteristics and thermal fluctuation characteristics suitable for higher density recording.

In the case where the magnetic layer 16 is formed of a plurality of magnetic layers, it is preferable to provide a nonmagnetic layer between the adjacent magnetic layers. In a case where the magnetic layer 16 is formed of three layers of the first magnetic layer, the second magnetic layer, and the third magnetic layer, it is preferable to provide a nonmagnetic layer between the first magnetic layer and the second magnetic layer and between the second magnetic layer and the third magnetic layer.

By providing the nonmagnetic layer with an appropriate thickness between the adjacent magnetic layers, the magnetization reversal of each film is facilitated, it is possible to reduce the dispersion of the magnetization reversal of the whole magnetic particles, and it is possible to further improve the S/N ratio.

For the nonmagnetic layer provided between the adjacent magnetic layers of the magnetic layer 16, it is possible to suitably use, for example. Ru, Ru alloy, CoCr alloy, CoCrX1 alloy (X1 represents one or two or more elements selected from Pt, Ta, Re, Ru, Cu, Nb, Ni, Mn, Ge, Si, O, N, W, Mo, Ti, V, Zr, and B) or the like.

It is preferable to use an alloy material including an oxide, a metal nitride, or a metal carbide for the nonmagnetic layer provided between the adjacent magnetic layers of the magnetic layer 16. Specifically, as the oxide, for example, it is possible to use $SiO_2$, $Al_2O_3$, $Ta_2O_5$, $Cr_2O_3$, MgO, $Y_2O_3$, $TiO_2$, or the like. As the metal nitride, for example, it is possible to use AlN, $Si_3N_4$, TaN, CrN, or the like. As the metal carbide, for example, it is possible to use TaC, BC, SiC, or the like.

It is possible to form the nonmagnetic layer by, for example, a sputtering method.

In order to realize a higher recording density, the magnetic layer 16 is preferably a perpendicular magnetic recording magnetic layer whose easy axis of magnetization is oriented perpendicular to the substrate surface. The magnetic layer 16 may be for in-plane magnetic recording.

The magnetic layer 16 may be formed by any method known in the related art, such as a vapor deposition method, an ion beam sputtering method, a magnetron sputtering method, or the like. The magnetic layer 16 is usually formed by a sputtering method.

[Protective Layer]

The protective layer 17 protects the magnetic layer 16. The protective layer 17 may be formed of one layer or may be formed of a plurality of layers. Examples of the material of the protective layer 17 include carbon, carbon including nitrogen, silicon carbide, and the like.

As a method for film-forming the protective layer 17, it is possible to use a sputtering method using a target material including carbon, a chemical vapor deposition (CVD) method using a hydrocarbon material such as ethylene or toluene, an ion beam deposition (IBD) method, or the like.

[Lubricating Layer]

The lubricating layer 18 prevents contamination of the magnetic recording medium 10. In addition, the lubricating layer 18 improves the durability of the magnetic recording medium 10 by reducing the frictional force of the magnetic head of the magnetic recording/reproducing apparatus sliding on the magnetic recording medium 10.

As shown in FIG. 1, the lubricating layer 18 is formed in contact with the protective layer 17. The lubricating layer 18 is formed by coating the lubricant for the magnetic recording medium of the embodiment described above on the protective layer 17. Therefore, the lubricating layer 18 includes the fluorine-containing ether compound described above.

In the case where the protective layer 17 arranged under the lubricating layer 18 is formed of carbon, carbon including nitrogen, or silicon carbide, the lubricating layer 18 is bonded with a high bonding force with the fluorine-containing ether compound included in the lubricating layer 18. As a result, even if the thickness of the lubricating layer 18 is reduced, it is easy to obtain the magnetic recording medium 10 in which the surface of the protective layer 17 is covered with a high coverage ratio, and it is possible to effectively prevent contamination of the surface of the magnetic recording medium 10.

The average film thickness of the lubricating layer 18 is preferably 0.5 nm (5 Å) to 2 nm (20 Å), more preferably 0.5 nm (5 Å) to 1.5 nm (15 Å).

When the average film thickness of the lubricating layer 18 is 0.5 nm or more, the lubricating layer 18 is formed with a uniform film thickness without being formed into an island shape or mesh shape. Therefore, it is possible for the lubricating layer 18 to cover the surface of the protective layer 17 with a high coverage ratio. In addition, setting the average film thickness of the lubricating layer 18 to 2 nm or less makes it possible to make the floating height of the magnetic head sufficiently small, and to increase the recording density of the magnetic recording medium 10.

In the case where the surface of the protective layer 17 is not covered with the lubricating layer 18 at a sufficiently high coverage ratio, environmental substances adsorbed on the surface of the magnetic recording medium 10 pass through the gap of the lubricating layer 18, and permeate under the lubricating layer 18. The environmental substances which permeated the lower layer of the lubricating layer 18 adsorb to and bond with the protective layer 17 to generate contaminants. Then, at the time of magnetic recording/reproduction, these contaminants (aggregated components) adhere (transfer) to the magnetic head as a smear, which damages the magnetic head and deteriorates the magnetic recording/reproducing characteristics of the magnetic recording/reproducing apparatus.

Examples of environmental substances which generate contaminants include hydrocarbons having relatively high molecular weights such as siloxane compounds (cyclic siloxanes and linear siloxanes), ionic impurities and octacosane, plasticizers such as dioctyl phthalate, and the like. Examples of the metal ions included in the ionic impurities include sodium ions, potassium ions, and the like. Examples of inorganic ions included in the ionic impurities include chlorine ions, bromine ions, nitrate ions, sulfate ions, ammonium ions, and the like. Examples of organic ions included in the ionic impurities include oxalic acid ions, formic acid ions, and the like.

[Method of Forming Lubricating Layer]

In order to form the lubricating layer 18, example methods include a method of preparing a magnetic recording medium in the manufacturing process of forming each layer up to the protective layer 17 on the substrate 11, and coating the lubricating layer-forming solution on the protective layer 17.

The lubricating layer-forming solution is obtained by diluting the lubricant for a magnetic recording medium of the embodiment described above with a solvent as necessary and setting a viscosity and a concentration suitable for the coating method. Examples of a solvent to be used for the lubricating layer-forming solution include a fluorine-based solvent such as Vertrel (registered trademark) XF (trade name, manufactured by Du Pont-Mitsui Fluorochemicals Co., Ltd.), and the like.

The method of coating the lubricating layer-forming solution is not particularly limited, and examples thereof include a spin coating method and a dipping method. In the case of using the dipping method, for example, it is possible to use the following method. First, the substrate 11 on which each layer up to the protective layer 17 is formed is immersed in a lubricating layer-forming solution placed in an immersion tank of a dip coating apparatus. Next, the substrate 11 is pulled up from the immersion tank at a predetermined speed. Due to this, the lubricating layer-forming solution is coated on the surface of the protective layer 17 on the substrate 11.

Using the dipping method, it is possible to uniformly coat the lubricating layer-forming solution on the surface of the protective layer 17, and to form the lubricating layer 18 with a uniform film thickness on the protective layer 17.

In the magnetic recording medium 10 of the present embodiment, at least a magnetic layer 16, a protective layer 17, and a lubricating layer 18 are sequentially provided on the substrate 11. In the magnetic recording medium 10 of the present embodiment, the lubricating layer 18 including the fluorine-containing ether compound described above is formed in contact with the protective layer 17. Even if the thickness of the lubricating layer 18 is reduced, it is possible to obtain excellent wear resistance, and suppress pick-up. Therefore, in the magnetic recording medium 10 of the present embodiment, it is possible to further reduce the floating height of the magnetic head by reducing the thickness of the lubricating layer 18.

In addition, in the magnetic recording medium 10, since deterioration due to friction and abrasion by the magnetic head is suppressed for a long period by the lubricating layer 18, good durability is obtained.

EXAMPLES

A more detailed description will be given below of the present invention with reference to Examples and Comparative Examples. Here, the present invention is not limited to only the following examples.

Synthesis Example 1

A fluoropolyether (number-average molecular weight 1,300, molecular weight distribution 1.1) (20.0 g) represented by $HOCH_2CF_2O(CF_2CF_2O)_x(CF_2O)_yCF_2CH_2OH$ (in the formula, x represents an integer of 1 to 15 and y represents an integer of 1 to 15), t-BuOH (tertiary butyl alcohol) (100.0 mL), and glycidyl-4-methoxyphenyl ether (manufactured by Sigma-Aldrich Co. LLC.) (2.8 g) were placed in a 300 mL eggplant-shaped flask under a nitrogen gas atmosphere and stirred until uniform. Furthermore, t-BuOK (potassium tertiary butoxide) (0.5 g) was added to the eggplant-shaped flask, heated to 70° C., and reacted by stirring for 18 hours. Thereafter, the obtained reaction product was cooled to 25° C., neutralized with hydrochloric acid, and then washed by adding a fluorine-based solvent (trade name: ASAHIKLIN (registered trademark) AK-225, manufactured by Asahi Glass Co., Ltd.). After the washing, the organic layer was recovered, dehydrated by adding sodium sulfate, and subjected to filter filtration. The solvent included in the filtrate was distilled off with an evaporator, and the residue was separated by column chromatography to obtain compound A (9.0 g) as a colorless transparent liquid.

$^1$H-NMR and $^{19}$F-NMR measurements of the obtained compound A were performed and the structure was identified based on the following results.

$^1$H-NMR (acetone-$D_6$): δ [ppm]=3.76 (3H), 3.88 to 4.21 (9H), 6.59 to 6.67 (2H), 6.70 to 6.80 (2H) $^{19}$F-NMR (acetone-$D_6$): δ [ppm]=−91.15 to −88.51 (24F), −83.30 (1F), −81.29 (1F), −80.65 (1F), −78.65 (1F), −55.65 to −51.59 (12F)

$^1$H-NMR measurement of the obtained compound B was carried out, and the structure was identified based on the following results.

$^1$H-NMR ($CDCl_3$): δ [ppm]=7.48 (1H), 7.35 (2H), 5.88 to 5.95 (1H), 5.21 to 5.32 (2H), 4.06 to 4.22 (4H), 3.59 to 3.67 (2H), 2.51 (1H)

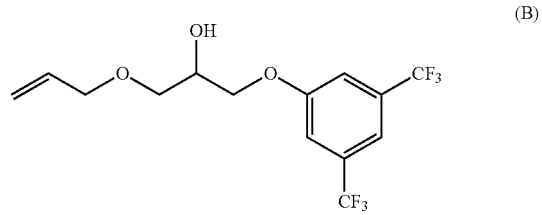
(B)

Compound B (7.3 g), dichloromethane (62.0 mL), and m-chloroperbenzoic acid (9.7 g) were placed into a 300 mL eggplant-shaped flask under ice cooling at 0° C. and, after stirring for 0.5 hours, the mixture was stirred at 25° C. for 24 hours. Furthermore, a saturated sodium hydrogencarbonate aqueous solution (20.0 mL) and a saturated sodium sulfite aqueous solution (20.0 mL) were added to the eggplant-shaped flask described above under ice cooling at 0° C., and, after stirring for 0.5 hours, the mixture was stirred at 25° C. for 0.5 hours and reacted. Sodium sulfate was added to the organic layer recovered by washing the reaction product, dehydrated, and then subjected to filtration. The solvent included in the filtrate was distilled off with an evaporator, and the residue was separated by column chromatography to obtain compound C (6.6 g) as a colorless transparent liquid.

$^1$H-NMR measurement of the obtained compound C was carried out, and the structure was identified based on the following results.

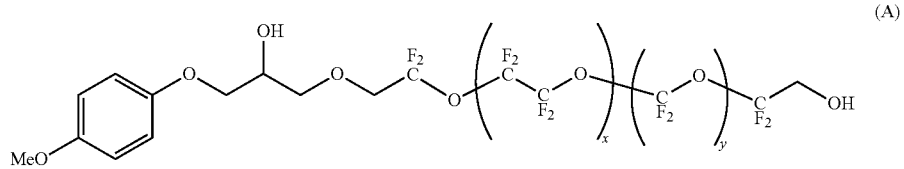
(A)

(In Formula (A), x represents an integer of 1 to 15, y represents an integer of 1 to 15, and Me represents a methyl group.)

3,5-bistrifluoromethylphenol (8.0 g), toluene (40.0 mL), and tetrabutylphosphonium bromide (0.35 g) were placed in a 100 mL eggplant-shaped flask under a nitrogen gas atmosphere and then stirred until uniform. Furthermore, allyl glycidyl ether (7.94 g) was added to the eggplant-shaped flask, heated to 110° C., and reacted by stirring for 6 hours. Thereafter, the obtained reaction product was cooled to 25° C., methylene chloride (20.0 mL) was added thereto, and saturated sodium hydrogencarbonate aqueous solution (20.0 mL) was added for cleaning and washing. After washing, the organic layer was recovered, dehydrated by adding sodium sulfate, and subjected to filter filtration. The solvent included in the filtrate was distilled off with an evaporator, and the residue was separated by column chromatography to obtain compound B (7.3 g) as a colorless transparent liquid.

$^1$H-NMR ($CDCl_3$): δ [ppm]=7.48 (1H), 7.35 (2H), 4.09 to 4.23 (3H), 3.88 to 3.92 (1H), 3.64 to 3.80 (2H), 3.43 to 3.49 (1H), 3.16 to 3.19 (1H), 2.82 to 2.84 (1H), 2.63 to 2.66 (2H)

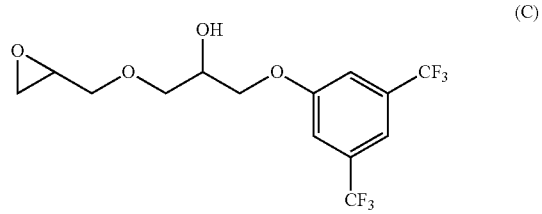 [SMILES: OC(COCC1CO1)COc1cc(C(F)(F)F)cc(C(F)(F)F)c1]
(C)

Compound A (4.0 g), t-BuOH (32.1 mL), and t-BuOK (0.07 g) were placed into a 200 mL eggplant-shaped flask under a nitrogen gas atmosphere and stirred until uniform. Furthermore, compound C (1.22 g) was added to the eggplant-shaped flask described above, heated to 70° C., and reacted by stirring for 24 hours. The reaction product was cooled to 25° C., and washed by adding ASAHIKLIN AK 225. After washing, the organic layer was recovered, dehydrated by adding sodium sulfate, and subjected to filter filtration. The filtrate was distilled off with an evaporator, and the residue was separated by column chromatography to obtain compound D (2.40 g) as a colorless and transparent liquid.

$^1$H-NMR and $^{19}$F-NMR measurements of the obtained compound D were carried out, and the structure was identified based on the following results.

$^1$H-NMR (acetone-$D_6$): δ [ppm]=7.47 (3H), 6.71 to 6.73 (2H), 6.60 to 6.61 (2H), 4.05 to 4.19 (7H), 3.92 to 3.96 (4H), 3.60 to 3.85 (11H) $^{19}$F-NMR (acetone-$D_6$): δ [ppm]=−90.85 to −88.49 (24F), −80.65 (2F), −78.64 (2F), −64.41 (6F), −55.36 to −51.80 (12F)

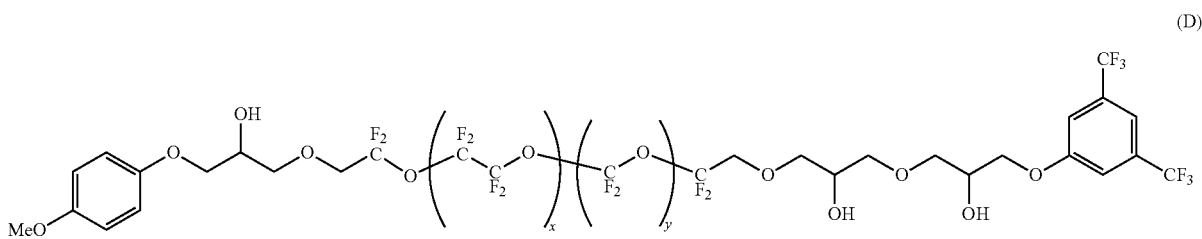

(D)

(In Formula (D), x represents an integer of 1 to 15, y represents an integer of 1 to 15, and Me represents a methyl group.)

Synthesis Example 2

The same fluoropolyether (25.2 g) as in Synthesis Example 1, t-BuOH (11.6 mL), and glycidyl-2-naphthyl ether (9.1 g) were placed in a 100 mL eggplant-shaped flask under a nitrogen gas atmosphere, and stirred until uniform. Furthermore, t-BuOK (1.1 g) was added to the eggplant-shaped flask described above, heated to 70° C., and reacted by stirring for 8 hours. Thereafter, the obtained reaction product was cooled to 25° C., neutralized with hydrochloric acid, and then washed by adding ASAHIKLIN AK 225. After washing, the organic layer was recovered, dehydrated by adding sodium sulfate, and subjected to filter filtration. The solvent contained in the filtrate was distilled off with an evaporator, and the residue was separated by column chromatography to obtain compound E (11.1 g) as a colorless transparent liquid.

$^1$H-NMR and $^{19}$F-NMR measurements of the obtained compound E were carried out and the structure was identified based on the following results.

$^1$H-NMR (acetone-$D_6$): δ [ppm]=3.86 to 4.06 (5H), 4.14 to 4.25 (4H), 7.09 to 7.11 (2H), 7.26 to 7.30 (1H), 7.36 to 7.39 (1H), 7.58 to 7.62 (3H) $^{19}$F-NMR (acetone-$D_6$): δ [ppm]=−90.91 to −88.60 (24F), −83.31 (1F), −81.30 (1F), −80.64 (1F), −78.65 (1F), −55.38 to −51.80 (12F)

(In Formula (E), x represents an integer of 1 to 15, and y represents an integer of 1 to 15.)

Compound E (9.3 g), t-BuOH (72.4 mL), and t-BuOK (0.22 g) were placed in a 200 mL eggplant-shaped flask under a nitrogen gas atmosphere and stirred until uniform. Furthermore, compound C (2.2 g) was added to the eggplant-shaped flask described above, heated to 70° C., and reacted by stirring for 9 hours. The reaction product was cooled to 25° C. and washed by adding ASAHIKLIN AK 225. After washing, the organic layer was recovered, dehydrated by adding sodium sulfate, and subjected to filter filtration. The solvent included in the filtrate was distilled off with an evaporator, and the residue was separated by column chromatography to obtain compound F (2.50 g) as a colorless and transparent liquid.

$^1$H-NMR and $^{19}$F-NMR measurements of the obtained compound F were carried out, and the structure was identified based on the following results.

$^1$H-NMR (acetone-$D_6$): δ [ppm]=7.59 to 7.63 (3H), 7.48 (3H), 7.37 to 7.40 (1H), 7.27 to 7.31 (1H), 7.10 to 7.13 (2H), 4.16 to 4.31 (8H), 4.03 to 4.12 (3H), 3.93 to 3.97 (2H), 3.68 to 3.85 (5H), 3.59 to 3.63 (1H) $^{19}$F-NMR (acetone-$D_6$): δ [ppm]=−91.10 to −88.91 (24F), −80.65 (2F), −78.64 (2F), −64.41 (6F), −55.36 to −51.81 (12F)

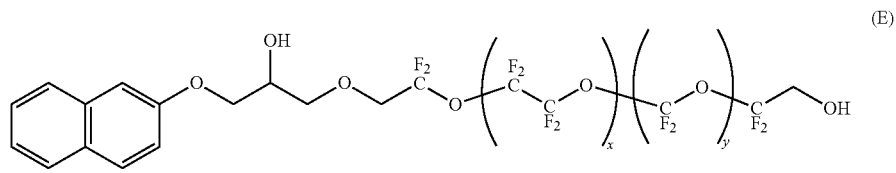

(E)

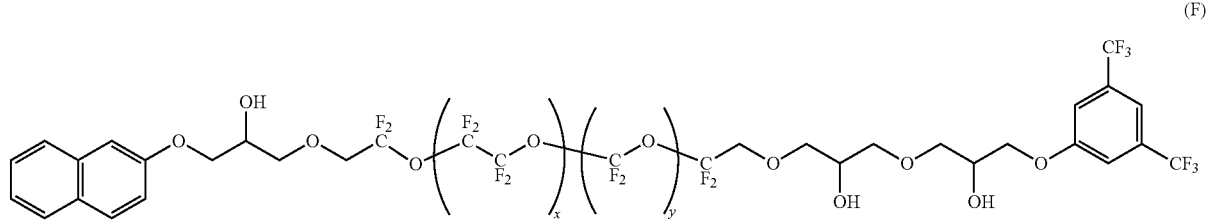

(F)

(In Formula (F), x represents an integer of 1 to 15, and y represents an integer of 1 to 15.)

Synthesis Example 3

Compound E (21.9 g), t-BuOH (146.5 mL), and t-BuOK (0.32 g) were placed in a 300 mL eggplant-shaped flask under a nitrogen gas atmosphere and stirred until uniform. Furthermore, glycidol (0.93 mL) was added to the eggplant-shaped flask described above, heated to 70° C., and reacted by stirring for 8 hours. The reaction product was cooled to 25° C. and washed by adding ASAHIKLIN AK 225. After washing, the organic layer was recovered, dehydrated by adding sodium sulfate, and subjected to filter filtration. The solvent included in the filtrate was distilled off with an evaporator, and the residue was separated by column chromatography to obtain compound G (9.52 g) as a colorless transparent liquid.

$^1$H-NMR and $^{19}$F-NMR measurements of the obtained compound G were carried out, and the structure was identified based on the following results.

$^1$H-NMR (acetone-$D_6$): δ [ppm]=3.44 to 3.51 (1H), 3.65 to 3.67 (1H), 3.71 to 3.73 (3H), 3.95 to 4.08 (3H), 4.15 to 4.26 (5H), 7.09 to 7.11 (2H), 7.26 to 7.30 (1H), 7.36 to 7.39 (1H), 7.58 to 7.62 (3H) $^{19}$F-NMR (acetone-$D_6$): δ [ppm]=−90.91 to −88.60 (24F), −81.30 (2F), −78.65 (2F), −55.38 to −51.80 (12F)

(In Formula (G), x represents an integer of 1 to 15, and y represents an integer of 1 to 15.)

Compound G (9.52 g), t-BuOH (70.8 mL), and glycidyl-2-naphthyl ether (1.79 g) were placed in a 200 mL eggplant-shaped flask under a nitrogen gas atmosphere and stirred until uniform. Furthermore, t-BuOK (1.09 g) was added to the eggplant-shaped flask described above, heated to 70° C., and reacted by stirring for 28 hours. Thereafter, the obtained reaction product was cooled to 25° C. neutralized with hydrochloric acid, and then washed by adding ASAHIKLIN AK 225. After washing, the organic layer was recovered, dehydrated by adding sodium sulfate, and subjected to filter filtration. The solvent contained in the filtrate was distilled off with an evaporator, and the residue was separated by column chromatography to obtain compound H (4.47 g) as a colorless and transparent liquid.

$^1$H-NMR and $^{19}$F-NMR measurements of the obtained compound H were carried out, and the structure was identified based on the following results.

$^1$H-NMR (acetone-$D_6$): δ [ppm]=7.42 to 7.63 (12H), 7.37 to 7.40 (2H), 7.27 to 7.31 (2H), 7.10 to 7.14 (4H), 4.10 to 4.32 (8H), 4.00 to 4.11 (3H), 3.89 to 3.92 (2H), 3.61 to 3.86 (5H), 3.59 to 3.62 (1H) $^{19}$F-NMR (acetone-$D_6$): δ [ppm]=−90.90 to −88.58 (24F), −81.28 (2F), −78.71 (2F), −55.41 to −51.82 (12F)

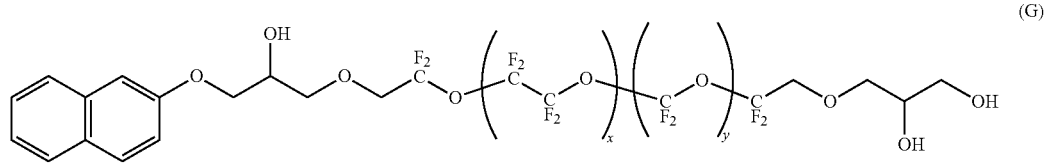

(G)

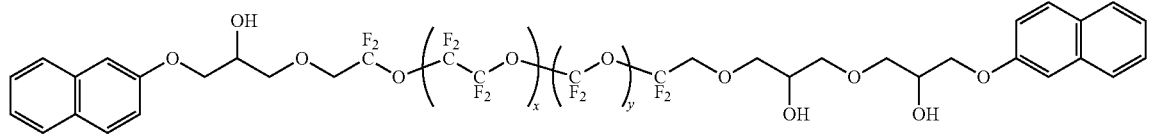

(In Formula (H), x represents an integer of 1 to 15, and y represents an integer of 1 to 15.)

Synthesis Example 4

The same fluoropolyether (30.0 g) as in Synthesis Example 1, 2-(bromomethyl) naphthalene (25.6 g), and N,N-diisopropylethylamine (15.0 g) were added to a 300 mL eggplant-shaped flask under a nitrogen gas atmosphere, heated to 60° C., and reacted by stirring for 24 hours. Thereafter, the obtained reaction product was cooled to 25° C., ASAHIKLIN AK 225 was added thereto and shaken, and then the remaining white solid was removed by filter filtration. The filtrate was collected, washed, and sodium sulfate was added to the recovered organic layer, followed by dehydration and filter filtration. The solvent contained in the filtrate was distilled off with an evaporator, and the residue was separated by column chromatography to obtain compound 1 (6.4 g) as a colorless and transparent liquid.

$^1$H-NMR and $^{19}$F-NMR measurements of the obtained compound I were carried out, and the structure was identified based on the following results.

$^1$H-NMR (acetone-D$_6$): δ [ppm]=3.90 (2H), 4.10 (2H), 4.97 (2H), 7.46 to 7.52 (3H), 7.71 to 7.77 (4H) $^{19}$F-NMR (acetone-D$_6$): δ [ppm]=−91.43 to −88.92 (24F), −83.30 (1F), −81.29 (1F), −80.18 (1F), −78.18 (1F), −55.37 to −51.83 (12F)

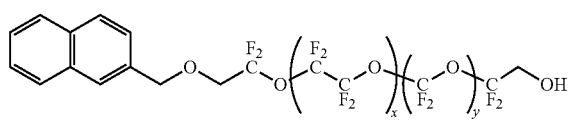

(In Formula (I), x represents an integer of 1 to 15, and y represents an integer of 1 to 15.)

Under ice cooling at 0° C., glycerol a, a diaryl ether (20.0 g), dichloromethane (340 mL), and m-chloroperbenzoic acid (63.4 g) were placed in a 500 mL eggplant-shaped flask, stirred for 0.5 hours, and then stirred for 12 hours at 25° C. Saturated sodium hydrogencarbonate aqueous solution (100.0 mL) and a saturated sodium sulfite aqueous solution (100.0 mL) were further added to the eggplant-shaped flask described above under ice cooling at 0° C., and after stirring for 0.5 hours, the mixture was reacted by stirring for 0.5 hours at 25° C. Sodium sulfate was added to the organic layer recovered by washing the reaction product, dehydrated, and then subjected to filtration. The solvent included in the filtrate was distilled off with an evaporator, and the residue was separated by column chromatography to obtain compound J (4.1 g) as a colorless transparent liquid.

$^1$H-NMR measurement of the obtained compound J was carried out, and the structure was identified based on the following results.

$^1$H-NMR (CDCl$_3$): δ [ppm]=3.96 to 4.00 (1H), 3.79 to 3.84 (2H), 3.50 to 3.65 (4H), 3.41 to 3.47 (2H), 3.14 to 3.17 (2H), 2.80 to 2.82 (2H), 2.61 to 2.63 (3H)

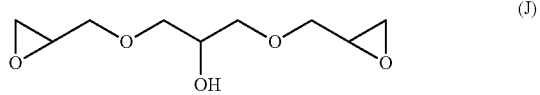 [SMILES: OC(COCC1CO1)COCC1CO1]

3,5-bistrifluoromethylphenol (1.2 g), toluene (52.0 mL), and tetrabutylphosphonium bromide (0.17 g) were placed in a 200 mL eggplant-shaped flask in a nitrogen gas atmosphere, and stirred until uniform. Furthermore, compound J (1.0 g) was added to the eggplant-shaped flask described above, heated to 110° C., and reacted by stirring for 8 hours. Thereafter, the obtained reaction product was cooled to 25° C., methylene chloride (20.0 mL) was added, and saturated sodium hydrogencarbonate aqueous solution (20.0 mL) was added for cleaning and washing. After washing, the organic layer was recovered, dehydrated by adding sodium sulfate, and subjected to filter filtration. The solvent contained in the filtrate was distilled off with an evaporator, and the residue was separated by column chromatography to obtain compound K (0.52 g) as a colorless transparent liquid.

$^1$H-NMR measurement of the obtained compound K was carried out, and the structure was identified based on the following results.

$^1$H-NMR (CDCl$_3$): δ [ppm]=7.48 (1H), 7.34 (2H), 4.10 to 4.23 (4H), 3.99 to 4.03 (1H), 3.84 to 3.88 (1H), 3.50 to 3.72 (7H), 3.39 to 3.43 (1H), 3.14 to 3.17 (1H), 2.80 to 2.82 (1H), 2.62 to 2.64 (1H)

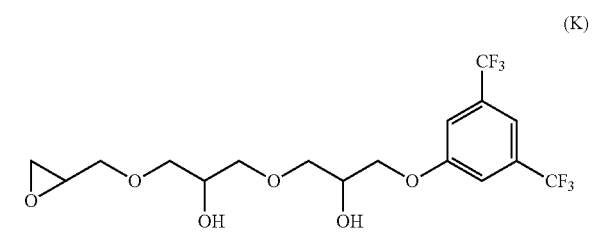 [SMILES: OC(COCC(O)COc1cc(C(F)(F)F)cc(C(F)(F)F)c1)COCC1CO1]

Compound I (1.82 g), t-BuOH (29.2 mL), and t-BuOK (0.05 g) were placed in a 200 mL eggplant-shaped flask under a nitrogen gas atmosphere and stirred until uniform. Furthermore, compound K (0.47 g) was added to the eggplant-shaped flask, heated to 70° C., and reacted by stirring for 9 hours. The reaction product was cooled to 25° C. and washed by adding ASAHIKLIN AK 225. After washing, the organic layer was recovered, dehydrated by adding sodium sulfate, and subjected to filter filtration. The solvent contained in the filtrate was distilled off with an evaporator, and the residue was separated by column chromatography to obtain compound L (0.42 g) as a colorless transparent liquid.

$^1$H-NMR and $^{19}$F-NMR measurements of the obtained compound L were carried out, and the structure was identified based on the following results.

$^1$H-NMR (acetone-D$_6$): δ [ppm]=7.72 to 7.77 (4H), 7.47 to 7.53 (6H), 4.98 (2H), 4.06 to 4.27 (6H), 3.83 to 3.88 (2H), 3.67 to 3.78 (5H), 3.48 to 3.65 (7H) $^{19}$F-NMR (acetone-D$_6$): δ [ppm]=−90.88 to −88.91 (24F), −80.71 (1F), −80.18 (1F), −78.68 (1F), −78.18 (1F), −55.37 to −51.82 (12F)

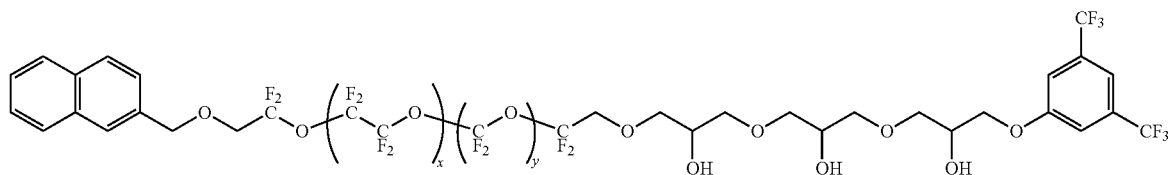

(L)

(In Formula (L), x represents an integer of 1 to 15, and y represents an integer of 1 to 15.)

Comparative Example 1

Fomblin Z-tetraol (molecular weight approximately 2,000) manufactured by Solvay Solexis represented by Formula (X) was used.

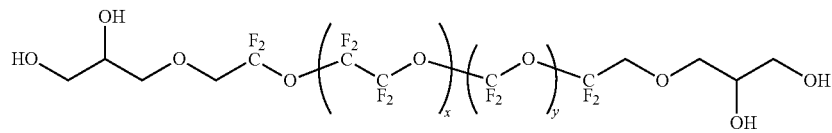

(X)

(In Formula (X), f represents an integer of 1 to 20, and g represents an integer of 1 to 20.)

Comparative Example 2

Compound Y was synthesized by the method described in Patent Document 2.

$^1$H-NMR and $^{19}$F-NMR measurements of the obtained compound Y were carried out, and the structure was identified based on the following results.

$^1$H-NMR (acetone-$D_6$): δ [ppm]=6.70 to 6.73 (2H), 6.59 to 6.61 (2H), 4.00 to 4.16 (5H), 3.92 to 3.96 (3H), 3.82 to 3.86 (1H), 3.72 to 3.77 (5H), 3.46 to 3.52 (1H) $^{19}$F-NMR (acetone-$D_6$): δ [ppm]=−92.25 to −90.29 (24F), −82.04 (2F), −80.04 (2F), −56.74 to −53.18 (12F)

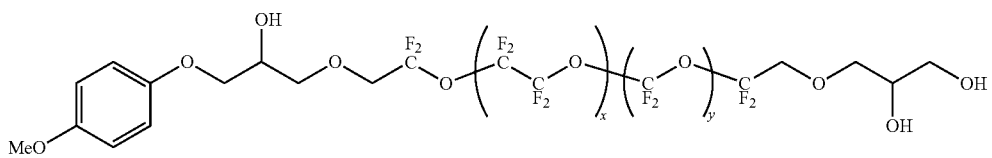

(Y)

(In Formula (Y), x represents an integer of 1 to 15, y represents an integer of 1 to 15, and Me represents a methyl group.)

Table 1 shows the structures of $R^1$ to $R^5$ when the compounds of Synthesis Examples 1 to 4 and Comparative Examples 1 and 2 thus obtained are applied to Formula (1). In addition, the number-average molecular weights of the compounds of Synthesis Examples 1 to 4 and Comparative Examples 1 and 2 were determined by the measurement of $^1$H-NMR and $^{19}$F-NMR described above. The results are shown in Table 1.

TABLE 1

| Compound | R$^1$ | R$^2$ | R$^3$ | R$^4$ | R$^5$ | Number-average Molecular Weight |
|---|---|---|---|---|---|---|
| Synthesis Example 1 | D | p-methoxyphenyl group | Formula (4) | Formula (3-1) m = 1 to 15, n = 1 to 15 | Formula (2) t = 2, k = 0 | 3,5-bistrifluoro-methylphenyl group | 1779 |
| Synthesis Example 2 | F | naphthyl group | Formula (4) | Formula (3-1) m = 1 to 15, n = 1 to 15 | Formula (2) t = 2, k = 0 | 3,5-bistrifluoro-methylphenyl group | 1799 |
| Synthesis Example 3 | H | naphthyl group | Formula (4) | Formula (3-1) m = 1 to 15, n = 1 to 15 | Formula (2) t = 2, k = 0 | naphthyl group | 1714 |
| Synthesis Example 4 | L | naphthylmethyl group | —O— | Formula (3-1) m = 1 to 15, n = 1 to 15 | Formula (2) t = 3, k = 0 | 3,5-bistrifluoro-methylphenyl group | 1761 |
| Comparative Example 1 | X | HO—CH$_2$(OH)—CH$_2$— | —O— | Formula (3-1) m = 1 to 15, n = 1 to 15 | Formula (2) t = 1, k = 0 | hydrogen atom | 2187 |
| Comparative Example 2 | Y | p-methoxyphenyl group | Formula (4) | Formula (3-1) m = 1 to 15, n = 1 to 15 | Formula (2) t = 1, k = 0 | hydrogen atom | 1565 |

Next, the lubricating layer-forming solution shown below was prepared by using the compounds obtained in Synthesis Examples 1 to 4 and Comparative Examples 1 and 2 by the method shown below. Using the obtained lubricating layer-forming solution, a lubricating layer of a magnetic recording medium was formed by the following method, and the magnetic recording media of Examples 1 to 4, Comparative Examples 1-1 and 1-2, and Comparative Example 2 were obtained.

[Lubricating Layer-Forming Solution]

The compounds obtained in Synthesis Examples 1 to 4 and Comparative Examples 1 and 2 were each dissolved in Vertrel (registered trademark) XF (trade name, manufactured by Du Pont-Mitsui Fluorochemicals Co., Ltd.), which is a fluorine-based solvent, the solution was diluted with Vertrel XF so as to have a film thickness of 9 Å to 13 Å when coated on the protective layer, and the lubricating layer-forming solutions of Examples 1 to 4. Comparative Examples 1-1 and 1-2, and Comparative Example 2 were prepared.

[Magnetic Recording Medium]

A magnetic recording medium was prepared in which an adhesive layer, a soft magnetic layer, a first underlayer, a second underlayer, a magnetic layer, and a protective layer were sequentially provided on a substrate having a diameter of 65 mm. The protective layer was formed of carbon.

Each of the lubricating layer-forming solutions of Examples 1 to 4. Comparative Examples 1-1 and 1-2, and Comparative Example 2 was coated by a dipping method onto the protective layer of the magnetic recording medium on which each of the layers up to the protective layer were formed. Here, the dipping method was carried out under conditions of an immersion speed of 10 mm/sec, a dipping time of 30 sec, and a pulling rate of 1.2 mm/sec.

Thereafter, the magnetic recording medium coated with the lubricating layer-forming solution was placed in a thermostat at 120° C. and heated for 10 minutes to remove the solvent in the lubricating layer-forming solution to form a lubricating layer on the protective layer and obtain a magnetic recording medium.

The film thicknesses of the lubricating layers of the magnetic recording media of Examples 1 to 4, Comparative Examples 1-1 and 1-2, and Comparative Example 2 thus obtained were measured by FT-IR (trade name: Nicolet iS 50, manufactured by Thermo Fisher Scientific Co., Ltd.). The results are shown in Tables 2 and 3.

TABLE 2

| | Compound | Film Thickness (Å) | Friction Coefficient Increase Time (sec) |
|---|---|---|---|
| Example 1 | D | 9.5 | 720 |
| Example 2 | F | 9.5 | 810 |
| Example 3 | H | 9.5 | 775 |
| Example 4 | L | 9.5 | 685 |
| Comparative Example 1-1 | X | 9.5 | 200 |
| Comparative Example 1-2 | X | 13 | 715 |
| Comparative Example 2 | Y | 9.5 | 670 |

TABLE 3

| | Compound | Film Thickness (Å) | Pick-up Evaluation |
|---|---|---|---|
| Example 1 | D | 9.5 | A |
| Example 2 | F | 9.5 | A |
| Example 3 | H | 9.5 | A |
| Example 4 | L | 9.5 | A |
| Comparative Example 1-1 | X | 9.5 | A |
| Comparative Example 2 | Y | 9.5 | C |

In addition, the wear resistance tests shown below were carried out on the magnetic recording media of Examples 1 to 4, Comparative Examples 1-1 and 1-2, and Comparative Example 2.

(Wear Resistance Test)

Using a pin-on-disk type friction wear tester, a ball of alumina having a diameter of 2 mm as a contact was slid on the lubricating layer of the magnetic recording medium at a load of 40 gf and a sliding speed of 0.25 m/sec and the friction coefficient of the surface of the lubricating layer was measured. Then, the sliding time until the friction coefficient of the surface of the lubricating layer abruptly increased was measured. The sliding time until the friction coefficient abruptly increased was measured four times for each lubricating layer of each magnetic recording medium and the average value (time) was used as an index of the wear resistance of the lubricant coating film. The results are shown in Table 2.

Here, it is possible to use the time until the friction coefficient abruptly increases as an index of the wear resistance of the lubricating layer for the reasons described below. This is because the abrasion of the lubricating layer of the magnetic recording medium progresses as the magnetic recording medium is used, and when the lubricating layer disappears due to abrasion, the contact and the protective layer are in direct contact with each other, and the friction coefficient abruptly increases.

As shown in Table 2, the magnetic recording media of Examples 1 to 4 and Comparative Example 2 were compared with the magnetic recording media (Comparative Examples 1-1 and 1-2) having a lubricating layer including the compound of Comparative Example 1, and in the case of the same film thickness (Comparative Example 1-1), the sliding time until the friction coefficient abruptly increased was long, and the wear resistance was good. In addition, for the magnetic recording medium having the lubricating layer including the compound of Comparative Example 1 to have the same wear resistance as those of the magnetic recording media of Examples 1 to 4 and Comparative Example 2, as shown in Comparative Example 1-2, it was necessary to make the film thickness as thick as 13 Å.

This is presumably because in the magnetic recording media of Examples 1 to 4, $R^1$ in the compound represented by Formula (1) forming the lubricating layer includes aromatic rings. In addition, the reason why the wear resistance of the magnetic recording medium having the lubricating layer including the compound of Comparative Example 2 is comparatively good is considered to be that $R^1$ in the compound represented by Formula (1) forming the lubricating layer includes an aromatic ring.

Next, the following pick-up suppression test was performed on the magnetic recording media of Examples 1 to 4, Comparative Example 1-1, and Comparative Example 2.

(Pick-Up Suppression Test)

A magnetic recording medium and a magnetic head were mounted on a spin stand, and the magnetic head was floated at a fixed point for 10 minutes under reduced pressure at room temperature (approximately 250 torr). Thereafter, the surface (the surface of the lubricating layer) of the magnetic head facing the magnetic recording medium was analyzed using an Electron Spectroscopy for Chemical Analysis (ESCA) analyzer. Then, the adhesion amount of the lubricant to the magnetic head was evaluated according to the criteria shown in Table 4 from the intensity of the fluorine-derived peak (signal intensity (a.u.)) measured by ESCA. The results are shown in Table 3.

TABLE 4

| Evaluation | Esca Signal Strength (a.u.) | Evaluation Criteria |
| --- | --- | --- |
| A | 500 or less | There was no lubricant adhered to the head and there was no change in the signal strength. |
| B | Over 500 to 1000 | There was a small amount of lubricant adhered to the head, and the signal strength was low. |
| C | Over 1000 | There was a large amount of lubricant adhered to the head, and the signal strength was high. |

As shown in Table 3, in the magnetic recording media of Examples 1 to 4 and Comparative Example 1-1, the pick-up suppression test result was better compared with the magnetic recording medium of Comparative Example 2.

From the results of Table 3, the pick-up suppressing effect in Examples 1 to 4 is presumed to be due to $R^4$ in the compound represented by Formula (1) forming the lubricating layer having two or three polar groups, and $R^5$ being an end group including an aromatic ring.

In addition, in Comparative Example 1-1, the reason for the favorable result of the pick-up suppression test is presumed to be that the compound of Comparative Example 1 forming the lubricating layer has four hydroxyl groups, such that the interaction with the protective layer is strong.

However, only the magnetic recording media of Examples 1 to 4 including the fluorine-containing ether compound of the present invention were excellent in the results of both the wear resistance test and the pick-up suppression test.

INDUSTRIAL APPLICABILITY

Using the lubricant for a magnetic recording medium including the fluorine-containing ether compound of the present invention makes it possible to form a lubricating layer having excellent wear resistance and capable of suppressing pick-up even when the thickness is reduced.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES

10 MAGNETIC RECORDING MEDIUM
11 SUBSTRATE
12 ADHESIVE LAYER
13 SOFT MAGNETIC LAYER
14 FIRST UNDERLAYER
15 SECOND UNDERLAYER
16 MAGNETIC LAYER
17 PROTECTIVE LAYER
18 LUBRICATING LAYER

What is claimed is:

1. A fluorine-containing ether compound represented by Formula (1), $$R^1-R^2-CH_2-R^3-CH_2-R^4-R^5 \quad (1)$$

in Formula (1), $R^1$ is any one selected from a benzene ring group which may have a substituent, a naphthalene ring group which may have a substituent, a benzyl group which may have a substituent, or a naphthylmethyl group which may have a substituent, $R^2$ is represented by —O— or Formula (4)

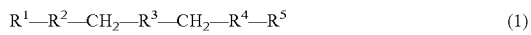

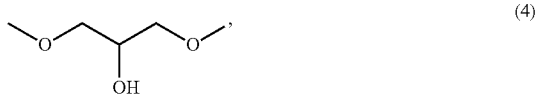

$R^3$ is a perfluoropolyether chain represented by any one of Formulas (3-1), (3-2), and (3-3),

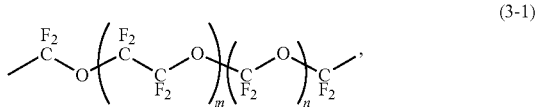

in Formula (3-1), m represents an integer of 1 to 30, and n represents an integer of 0 to 30,

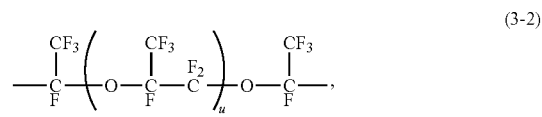

in Formula (3-2), u represents an integer of 1 to 30,

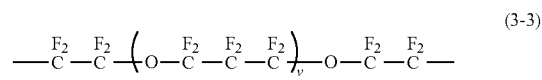

in Formula (3-3), v represents an integer of 1 to 30, $R^4$ is represented by Formula (2)

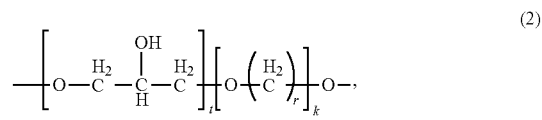

in Formula (2), t represents an integer of 2 or 3, r represents an integer of 1 to 4, and k represents an integer of 0 to 3, and $R^5$ is any one selected from a benzene ring group which may have a substituent, a naphthalene ring group which may have a substituent, a benzyl group which may have a substituent, or a naphthylmethyl group which may have a substituent.

2. The fluorine-containing ether compound according to claim 1, wherein the compound in Formula (1) is represented by Formula (5),

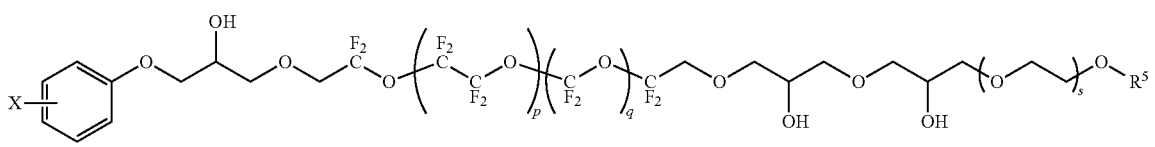

in Formula (5), X represents any one of a hydrogen atom, a halogen atom, an alkyl group having 1 to 5 carbon atoms, an alkoxy group having 1 to 5 carbon atoms, and a fluoroalkyl group having 1 to 5 carbon atoms, and may be one or plural and, when plural, X may be the same or different from each other, $R^5$ represents any one selected from a benzene ring group which may have a substituent, a naphthalene ring group which may have a substituent, a benzyl group which may have a substituent, or a naphthylmethyl group which may have a substituent, p represents an integer of 1 to 30, q represents an integer of 0 to 30, and s represents an integer of 0 to 3.

3. The fluorine-containing ether compound according to claim 1, wherein the compound in Formula (1) is represented by Formula (6), (6)

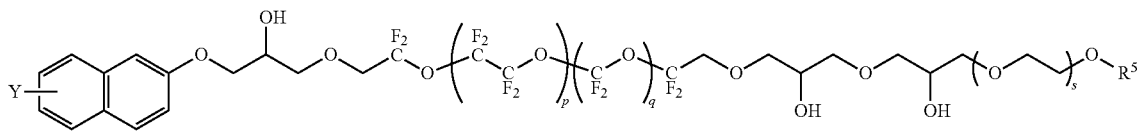

in Formula (6), Y represents any one of a hydrogen atom, a halogen atom, an alkyl group having 1 to 5 carbon atoms, an alkoxy group having 1 to 5 carbon atoms, and a fluoroalkyl group having 1 to 5 carbon atoms, and may be one or a plurality and, when a plurality, Y may be the same or different from each other, $R^5$ represents any one selected from a benzene ring group which may have a substituent, a naphthalene ring group which may have a substituent, a benzyl group which may have a substituent, or a naphthylmethyl group which may have a substituent, p represents an integer of 1 to 30, q represents an integer of 0 to 30, and s represents an integer of 0 to 3.

4. The fluorine-containing ether compound according to claim 1,
wherein the compound in Formula (1) is represented by Formula (7), (7)

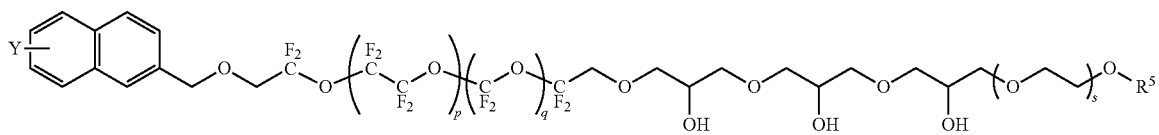

in Formula (7), Y represents any one of a hydrogen atom, a halogen atom, an alkyl group having 1 to 5 carbon atoms, an alkoxy group having 1 to 5 carbon atoms, and a fluoroalkyl group having 1 to 5 carbon atoms, and may be one or a plurality and, when a plurality, Y may be the same or different from each other, $R^5$ represents an aryl group or an aralkyl group, p represents an integer of 1 to 30, q represents an integer of 0 to 30, and s represents an integer of 0 to 3.

5. The fluorine-containing ether compound according to claim 1,
wherein a number-average molecular weight is in a range of 500 to 10,000.

6. A lubricant for a magnetic recording medium, comprising:
the fluorine-containing ether compound according to claim 1.

7. A magnetic recording medium, comprising:
at least a magnetic layer;
a protective layer; and
a lubricating layer sequentially provided on a substrate,
wherein the lubricating layer includes the fluorine-containing ether compound according claim 1.

8. The magnetic recording medium according to claim 7,
wherein an average film thickness of the lubricating layer is 0.5 nm to 2 nm.

9. The fluorine-containing ether compound according to claim 1, wherein in Formula (2), t represents an integer of 3.

10. The fluorine-containing ether compound according to claim 1, wherein the compound in Formula (1) is represented by Formula (8), (8)

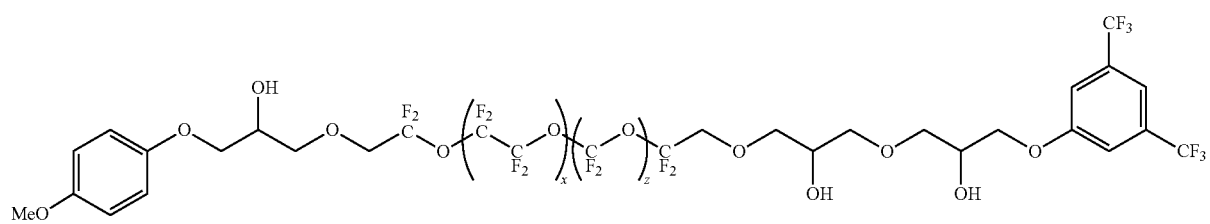

In Formula (8), x represents an integer of 1 to 15, z represents an integer of 0 to 15, and Me represents a methyl group.

11. The fluorine-containing ether compound according to claim 1, wherein the compound in Formula (1) is represented by Formula (9),

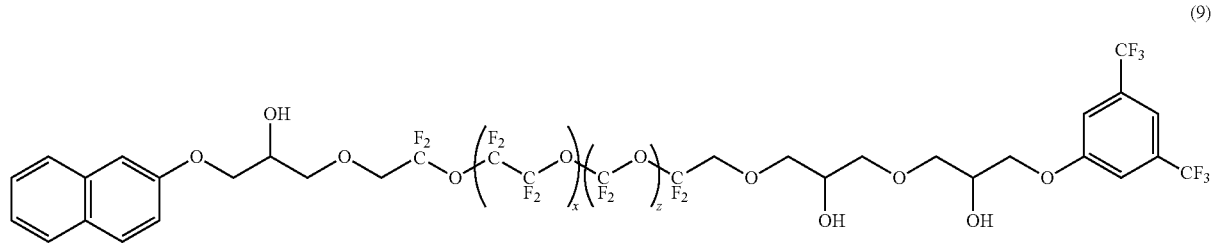

(9)

In Formula (9), x represents an integer of 1 to 15, and z represents an integer of 0 to 15.

12. The fluorine-containing ether compound according to claim 1, wherein the compound in Formula (1) is represented by Formula (11),

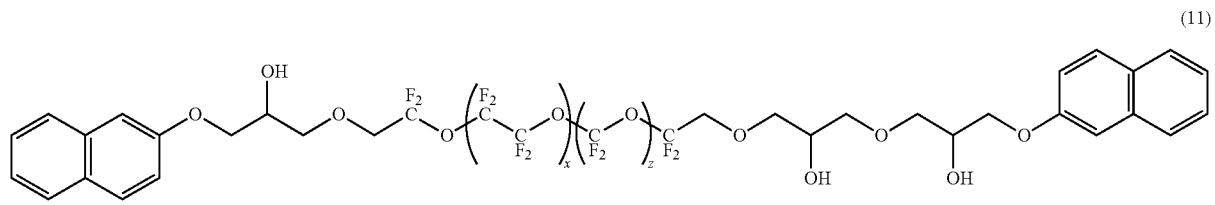

(11)

In Formula (11), x represents an integer of 1 to 15, and z represents an integer of 0 to 15.

* * * * *